United States Patent
Jung et al.

(10) Patent No.: US 7,939,550 B2
(45) Date of Patent: May 10, 2011

(54) AMINOPYRAZOLE DERIVATIVES, PROCESS FOR THE PREPARATION THEREOF, AND COMPOSITION FOR PREVENTING OR TREATING ISCHEMIC DISEASES CONTAINING THE SAME

(75) Inventors: Yong-Sam Jung, Daejeon (KR); Eunhee Kim, Daejeon (KR); Nakjeong Kim, Daejeon (KR); Yun-Suk Lee, Daejeon (KR); Jeehee Suh, Daejeon (KR); Haeyoung Suh, Suwon-si (KR); Kyu Yang Yi, Daejeon (KR); Sung-eun Yoo, Gongju-si (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 127 days.

(21) Appl. No.: 12/447,394

(22) PCT Filed: Oct. 26, 2007

(86) PCT No.: PCT/KR2007/005311
§ 371 (c)(1),
(2), (4) Date: Apr. 27, 2009

(87) PCT Pub. No.: WO2008/051047
PCT Pub. Date: May 2, 2008

(65) Prior Publication Data
US 2010/0063106 A1    Mar. 11, 2010

(30) Foreign Application Priority Data
Oct. 27, 2006   (KR) .................. 10-2006-0105183

(51) Int. Cl.
*A61K 31/44*   (2006.01)
*A61K 31/415*  (2006.01)
*C07D 231/00*  (2006.01)

(52) U.S. Cl. .................... 514/341; 514/407; 548/371.4

(58) Field of Classification Search .................. 514/341, 514/407; 548/371.4
See application file for complete search history.

(56) References Cited

U.S. PATENT DOCUMENTS
2005/0209297 A1   9/2005   Sanner et al.

FOREIGN PATENT DOCUMENTS
| WO | 02/072576 A1 | 9/2002 |
| WO | 2005/051919 A1 | 6/2005 |
| WO | 2006/023844 A2 | 3/2006 |
| WO | 2006/085685 A1 | 8/2006 |

*Primary Examiner* — Brandon J Fetterolf
*Assistant Examiner* — Christopher R Stone
(74) *Attorney, Agent, or Firm* — Sughrue Mion, PLLC

(57) ABSTRACT

Provided are aminopyrazole derivatives, a process for the preparation thereof, and a composition for preventing or treating an ischemic disease containing the same. Since the aminopyrazole derivatives of the present invention can reduce an ischemic cell death significantly, they can be effectively used for the prevention and treatment of ischemic diseases mediated by ischemic cell death, or protection of organs.

5 Claims, 1 Drawing Sheet

AMINOPYRAZOLE DERIVATIVES, PROCESS FOR THE PREPARATION THEREOF, AND COMPOSITION FOR PREVENTING OR TREATING ISCHEMIC DISEASES CONTAINING THE SAME

This is a national stage application under 35 U.S.C. §371 of PCT/KR2007/005311 filed on Oct. 26, 2007, which claims priority from Korean patent application 10-2006-0105183 filed on Oct. 27, 2006, all of which are incorporated herein by reference.

FIELD OF THE INVENTION

The present invention relates to aminopyrazole derivatives, a process for the preparation thereof, and a composition for preventing or treating ischemic diseases containing the same.

BACKGROUND OF THE INVENTION

Ischemia means a reduction in blood flow to organs, tissues or a region thereof, caused by contraction or occlusion of blood vessel. Once ischemia occurs, even if reperfusion, it is followed by various sequelas are developed due to the damage of nerve cells. Such ischemia is frequently occurs in coronary artery diseases, cardiovascular diseases, angina pectoris, headache or other symptoms related to blood vessel, and leads to irreversible damage, i.e., necrosis of cells or tissues, at last.

Since the ischemic diseases such as myocardial infarction, arrhythmia or heart failure caused by the cell damage and dysfunction during ischemia-reperfusion have a high morbidity rate, a high mortality rate, and a low complete cure rate, basic researches and clinic studies have been intensively undergone on this field last fifty years [Wang, Q. D. et al., Cardiovasc. Res. 55:25-37, 2002]. Especially, since ischemia-reperfusion injury is involved in various physiological mechanisms including the change of metabolism, immune response and ion homeostasis, generation of oxygen free radicals and the like, studies have actively undergoing on various fields related to immune modulators, cell death suppressors, ion channel modulators, etc. [Hearse, D. J. et al., Mol. Cell. Biochem. 186:177-184, 1998]. Based on such mechanismic researches, there have been developed a number of therapeutics and surgical operations focused on novel acting site so far, but the technique for protecting cardiomyocytes from ischemia-reperfusion injury has not yet been commercialized. Therefore, there is a need for an agent for preventing and treating ischemic heart diseases or a heart protecting agent, which can delay the progress of ischemic damage of cardiomyocytes and reduce reperfusion-induced injuries.

In addition, it has become obvious that if ischemia is disappeared by recovery of blood flow, the generation of reactive oxygen species (ROS) is accelerated, which causes a remarkable decrease of glutathione and brings about more serious diseases. Similar diseases are observed when blood flow stops or recovers during the transplant surgery of various kinds of organs such as heart, liver, lung, pancreas or blood vessel, and will be a problem in incising and removing an organ as well. A reactive oxygen and reactive free radicals assumed to cause diseases, are detected in the cytoplasm and organelle of cells consisting of tissues, especially in mitochondria producing ATP as a main energy source of a cell. In mitochondria, it is observed that the above reactive molecules are mainly released through a respiratory chain, and their concentration is significantly increased during ischemia-reperfusion.

In this regard, since ischemia leads to cell death or necrosis of cells, and especially cell death occurring after reperfusion is a main cause for tissue damage, ischemic cell death is a cause for various ischemic diseases comprising brain ischemia, heart ischemia, diabetic cardiovascular disease, heart failure, myocardial hypertrophy, retinal ischemia, ischemic colitis and ischemic acute renal failure.

In brain ischemia, the depletion of an energy source due to the reduction of blood supply induces ischemic cell death. Then, the ischemic cell death activates a receptor of cell membrane excessively, which is followed by various biochemical alterations including accumulation of glutamic acid and calcium respectively outside and inside of cells, and damage of lipid, protein and nucleic acid, and finally leads to brain tissue injury (Liu, P. K., J. Biomed. Sci. 10:4-13, 2003; Lipton, P., Physiol. Rev. 79:1431-1568, 1999; and Renolleau, S. et al., Stroke 29:1454-1460, 1998).

In case of myocardial infarction, heart failure and arrhythmia as ischemic heart diseases, it has been reported that ischemic cell death occurs by activation of lipid enzyme triggering damages of cell membranes, the changes of pH and calcium transport [Ferrari, R. Rev. Port. Cardiol. 5:7-20, 2000; Webster, K. A. et al., J. Clin. Invest. 104:239-252, 1999; Katz, A. M. et al., J. Mol Cell. Cardiol. 2:11-20, 1985; and Vandeplassche, G. et al., Basic Res. Cardiol. 85:384-391, 1990]. In retinal ischemia, it has been known that cell death of retinal cells mediated by glutamate is concerned with ischemic cell death [Napper, G. A. et al., Vis. Neurosci. 16:149-158, 1999]. Insufficient blood supply to colon causes ischemic cell death, and then, occlusive injury of arteries due to cell necrosis and hemodynamic disorders lead to ischemic colitis as an ischemic disease [Saegesser, F. et al., Pathobiol. Annu. 9:303-337, 1979].

Meanwhile, Minocycline, which is one of the tetracycline antibiotics inhibiting ischemic cell death, has been known to be effective in ischemic diseases such as cerebral infarction [Yrjanheikki, J. et al., Proc. Natl. Acad. Sci. USA 96:13496-13500, 1999], myocardial infarction [Scarabelli, T. M. et al., J. Am. Coll. Cardiol. 43:865-874, 2004] and an ischemic acute renal failure [Wang, J. et al., J. Biol. Chem. 279:19948-19954, 2004], from which it can be known that ischemic cell death is a cause of the above diseases.

Further, it has been known that damage or cell death of nerve cells, induced by ischemia is a main cause of various nervous diseases such as stroke, head trauma, Alzheimer's disease, Parkinson's disease, neonatal hypoxia, glaucoma or diabetic neuropathy [G. J. Zoppo et al., Drugs 54, 9 (1997); I. Sziraki et al., Neurosci. 85, 1101 (1998)].

Based on the intensive research on the development of compounds having pharmacological effect on the above ischemic diseases, the present inventors completed this invention by confirming that novel aminopyrazole derivatives inhibit ischemic cell death, and thus, can be used as an agent for preventing and treating ischemic diseases such as brain ischemia, heart ischemia, diabetic cardiovascular disease, heart failure, myocardial hypertrophy, retinal ischemia, ischemic colitis, ischemic acute renal failure, stroke, head trauma, Alzheimer's disease, Parkinson's disease, neonatal hypoxia, glaucoma and diabetic neuropathy, which are mediated by ischemic cell death, and an agent for protecting organs.

SUMMARY OF THE INVENTION

Therefore, it is an object of the present invention to provide novel aminopyrazole derivatives and a process for the preparation thereof.

It is another object of the present invention to provide a composition for preventing and treating ischemic diseases containing the aminopyrazole derivatives.

It is a further object of the present invention to provide a composition for protecting organs containing the aminopyrazole derivatives.

BRIEF DESCRIPTION OF THE DRAWING

The above and other objects and features of the present invention will become apparent from the following description of the invention, when taken in conjunction with the accompanying drawing below.

DETAILED DESCRIPTION OF THE INVENTION

Figure 1:
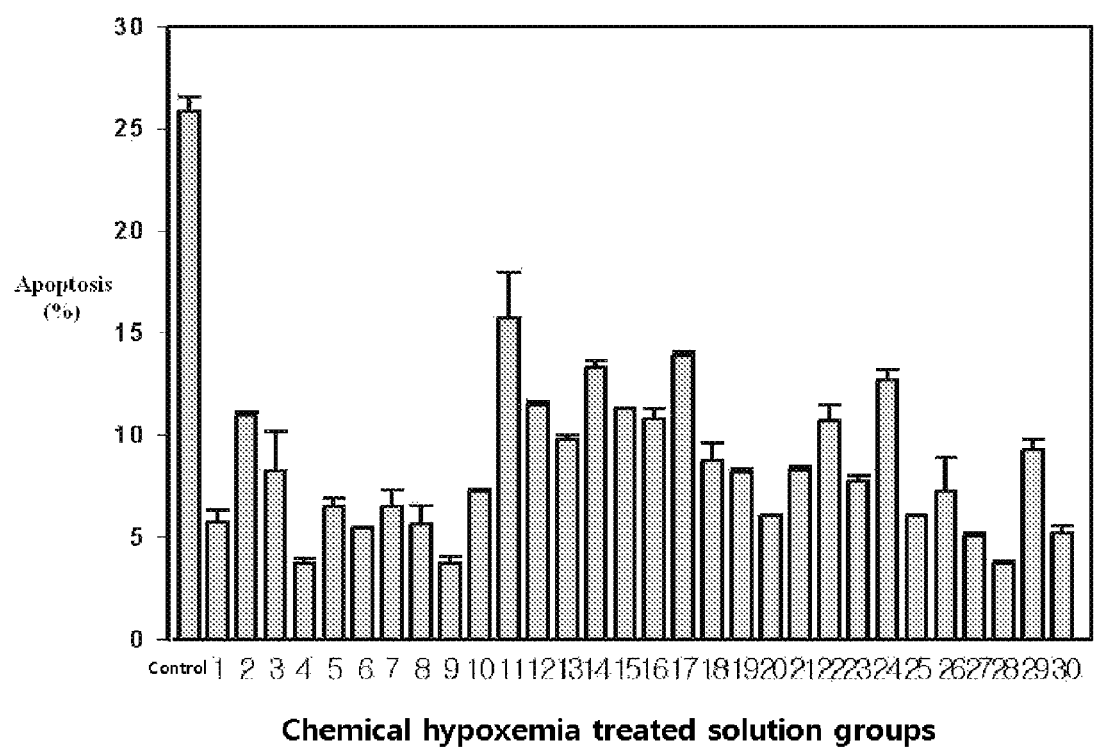
FIG. 1 illustrates the experimental data that the inhibition of hypoxemia-induced ischemic cell death by the aminopyrazole derivatives of the present invention was determined as the degree of cell death.

The present invention pertains to aminopyrazole derivatives represented by the following Formula 1 and pharmaceutically acceptable salts thereof:

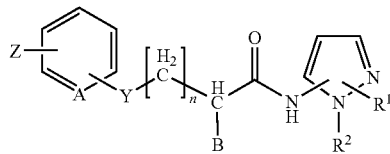

Formula 1 wherein
$R^1$ is —$CO_2R^3$, —$CH_2OR^3$, —$CONR^3R^4$ or

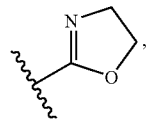

wherein $R^3$ and $R^4$ are, independently of each other, H, or straight, branched or cyclic $C_1$-$C_6$ alkyl;
$R^2$ is —$(CH_2)_mAr$, or straight, branched or cyclic $C_1$-$C_6$ alkyl wherein m is an integer of 1 to 3, Ar is phenyl, or $C_1$-$C_3$ alkyl or halogen substituted phenyl;
B is H, phenyl, or $C_1$-$C_3$ alkyl or halogen substituted phenyl;
N is an integer of 0 to 2;
Y is S, O, C, SO, $SO_2$ or $NR^3R^4$ wherein $R^3$ and $R^4$ are, independently of each other, H, or straight, branched or cyclic $C_1$-$C_6$ alkyl;
Z is H, halogen, $OCH_3$, $NO_2$, $NH_2$, or straight or branched $C_1$-$C_3$ alkyl; and
A is CH or N.

In accordance with said another object, the present invention provides a method for preparing the aminopyrazole derivatives.

In accordance with said another object, the present invention provides a composition for preventing or treating ischemic diseases containing the aminopyrazole derivatives or the pharmaceutically acceptable salts thereof.

In accordance with said another object, the present invention provides a composition for protecting organs containing the aminopyrazole derivatives or the pharmaceutically acceptable salts thereof.

The present invention is directed to aminopyrazole derivatives, a process for the preparation thereof, and a composition for preventing or treating ischemic diseases containing the same.

In Formula 1, preferably,
$R^1$ is —$CO_2R^3$, —$CH_2OR^3$, —$CONR^3R^4$ or

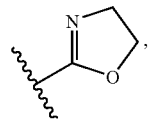

wherein $R^3$ and $R^4$ are, independently of each other, H, methyl or ethyl;
$R^2$ is —$(CH_2)_mAr$ wherein m is an integer of 1 to 3, Ar is phenyl, or $C_1$-$C_3$ alkyl or halogen substituted phenyl;
B is H, phenyl, or $C_1$-$C_3$ alkyl or halogen substituted phenyl;
N is 0 or 1;
Y is S, O, C, SO, $SO_2$ or $NR^3R^4$ wherein $R^3$ and $R^4$ are, independently of each other, H, or straight, branched or cyclic $C_1$-$C_6$ alkyl;
Z is H, halogen, $OCH_3$, $NO_2$, $NH_2$, or straight or branched $C_1$-$C_3$ alkyl; and
A is CH or N.

The aminopyrazole derivatives of the present invention may not be in only the form of their pharmaceutically acceptable salts but also in the form of solvates, hydrates and enantiomers thereof to be produced therefrom.

The pharmaceutically acceptable salts of the aminopyrazole derivatives of the present invention include acid addition salts prepared from pharmaceutically acceptable free acids. The free acids may be inorganic or organic. Examples of the organic acids include citric acid, maleic acid, fumaric acid, gluconic acid, methane sulfonic acid, acetic acid, glycolic acid, succinic acid, tartaric acid, 4-toluenesulfonic acid, galacturonic acid, embonic acid, glutamic acid and aspartic acid. Further, hydrochloric acid, hydrobromic acid, sulfuric acid, sulfurous acid or phosphoric acid, preferably methane sulfonic acid and hydrochloric acid may be used as inorganic acids.

Acid addition salts according to the present invention may be prepared using a conventional method, for example, by dissolving the aminopyrazole derivatives of Formula 1 in a water-miscible organic solvent such as acetone, methanol, ethanol and acetonitrile, adding an excess of an organic acid or an aqueous inorganic acid solution so as to precipitate or crystallize salts, evaporating solvent or excessive acids from the resulting mixture and drying or suction filtering the precipitated salts.

Examples of more preferable aminopyrazole derivatives according to the present invention are as following, and the respective structural formula thereof is listed in Table 1 below:
1) 4-[2-(4-bromo-phenylsulfanyl)-acetylamino]-1-phenethyl-1H-pyrazole-3-carboxylic acid methyl ester;

2) 4-[2-(phenylsulfanyl)-acetylamino]-1-phenethyl-1H-pyrazole-3-carboxylic acid methyl ester;
3) 4-[2-(3-methoxy-phenylsulfanyl)-acetylamino]-1-phenethyl-1H-pyrazole-3-carboxylic acid methyl ester;
4) 4-[2-(4-nitro-phenylsulfanyl)-acetylamino]-1-phenethyl-1H-pyrazole-3-carboxylic acid methyl ester;
5) 4-[2-(2-amino-phenylsulfanyl)-acetylamino]-1-phenethyl-1H-pyrazole-3-carboxylic acid methyl ester;
6) 4-[2-(4-methyl-phenylsulfanyl)-acetylamino]-1-phenethyl-1H-pyrazole-3-carboxylic acid methyl ester;
7) 4-[2-(4-fluoro-phenylsulfanyl)-acetylamino]-1-phenethyl-1H-pyrazole-3-carboxylic acid methyl ester;
8) 4-[2-(2-pyridylsulfanyl)-acetylamino]-1-phenethyl-1H-pyrazole-3-carboxylic acid methyl ester;
9) 4-[2-(2-pyridylsulfinyl)-acetylamino]-1-phenethyl-1H-pyrazole-3-carboxylic acid methyl ester;
10) 4-[2-(2-pyridylsulfonyl)-acetylamino]-1-phenethyl-1H-pyrazole-3-carboxylic acid methyl ester;
11) 4-[2-(3,4-dimethyl-phenylsulfanyl)-acetylamino]-1-phenethyl-1H-pyrazole-3-carboxylic acid methyl ester;
12) 4-[2-(4-bromo-phenylsulfanyl)-acetylamino]-1-benzyl-1H-pyrazole-3-carboxylic acid methyl ester;
13) 4-[2-phenylsulfanylacetylamino]-1-benzyl-1H-pyrazole-3-carboxylic acid methyl ester;
14) 4-[2-(4-bromo-phenylsulfanyl)-acetylamino]-1-methyl-1H-pyrazole-3-carboxylic acid methyl ester;
15) 4-[2-phenylsulfanylacetylamino]-1-methyl-1H-pyrazole-3-carboxylic acid methyl ester;
16) 4-[2-(4-bromo-phenylsulfanyl)-acetylamino]-2-phenethyl-2H-pyrazole-3-carboxylic acid methyl ester;
17) 4-[2-(4-bromo-phenylsulfanyl)-acetylamino]-2-methyl-2H-pyrazole-3-carboxylic acid methyl ester;
18) 4-[3-(4-bromo-phenylsulfanyl)-acetylamino]-1-phenethyl-1H-pyrazole-3-carboxylic acid methyl ester;
19) 5-[2-(4-bromo-phenylsulfanyl)-acetylamino]-1-phenethyl-1H-pyrazole-4-carboxylic acid ethyl ester;
20) 4-[2-(4-bromo-phenylsulfanyl)-2-phenyl-acetylamino]-1-phenethyl-1H-pyrazole-3-carboxylic acid methyl ester;
21) 5-[2-(4-bromo-phenylsulfanyl)-acetylamino]-1-methyl-1H-pyrazole-3-carboxylic acid methyl ester;
22) 1-methyl-5-(2-phenylsulfanyl-acetylamino)-1H-pyrazole-3-carboxylic acid methyl ester;
23) 4-[2-(4-bromo-phenylsulfanyl)-acetylamino]-1-phenethyl-1H-pyrazole-3-carboxylic acid;
24) 2-(4-bromo-phenylsulfanyl)-N-[3-(4,5-dihydro-oxazol-2-yl)-1-phenethyl-1H-pyrazol-4-yl]-acetamide;
25) 4-[2-(4-bromo-phenylsulfanyl)-acetylamino]-1-phenethyl-1H-pyrazole-3-carboxylic acid amide;
26) 2-(4-bromo-phenylsulfanyl)-N-(3-hydroxymethyl-1-phenethyl-1H-pyrazol-4-yl)-acetamide;
27) 4-[3-phenyl-propionylamino]-1-phenethyl-1H-pyrazole-3-carboxylic acid methyl ester;
28) 4-[2-(4-bromo-phenoxy)-acetylamino]-1-phenethyl-1H-pyrazole-3-carboxylic acid methyl ester;
29) 4-[2-(4-bromo-phenylamino)-acetylamino]-1-phenethyl-1H-pyrazole-3-carboxylic acid methyl ester; and
30) 2-(4-bromo-phenylsulfanyl)-N-(3-methoxymethyl-1-phenethyl-1H-pyrazol-4-yl)-acetamide.

TABLE 1

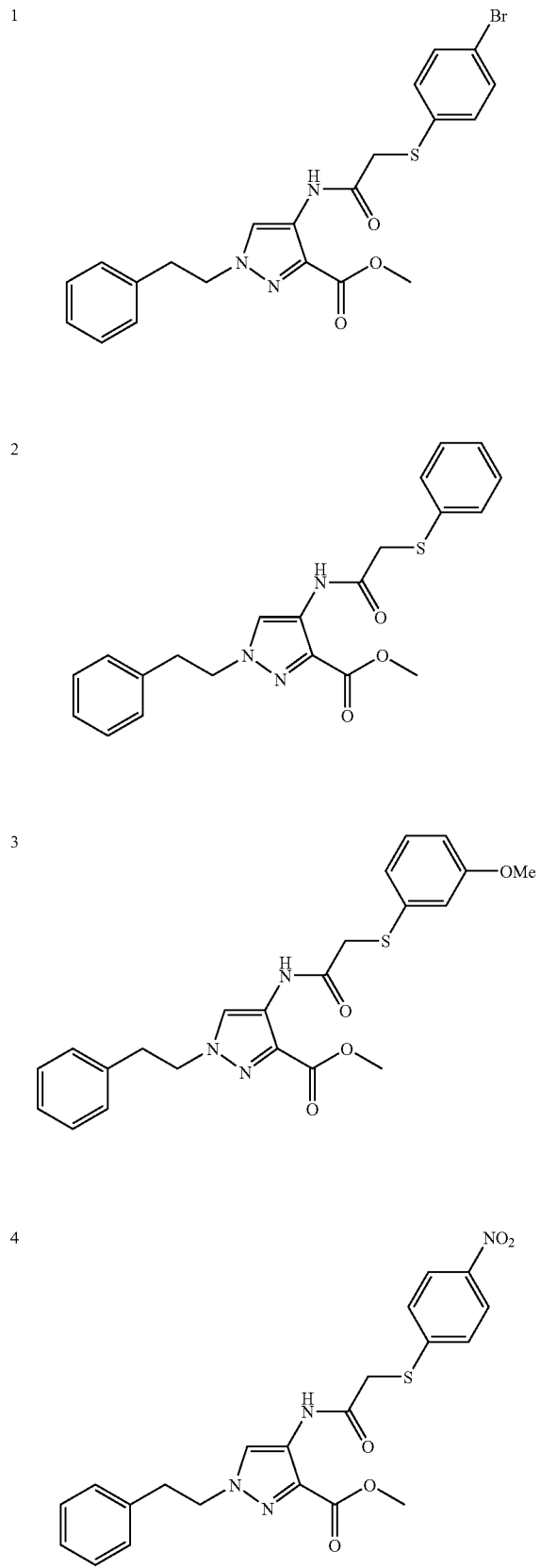

TABLE 1-continued
5
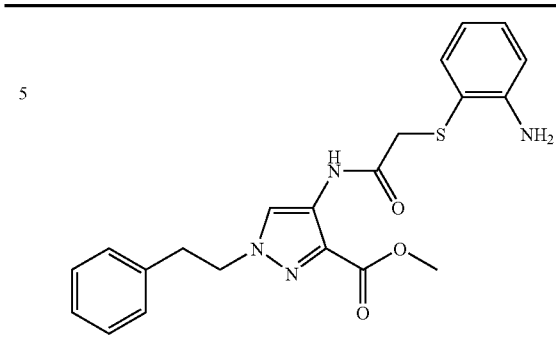
6
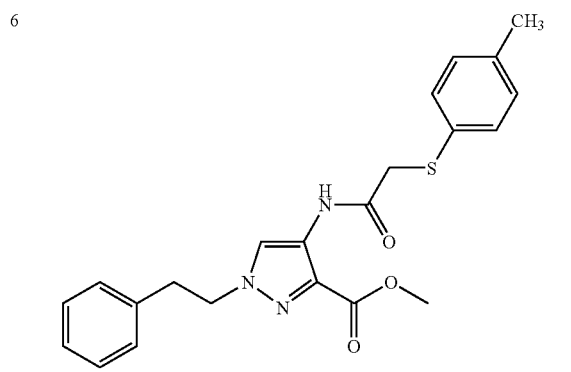
7
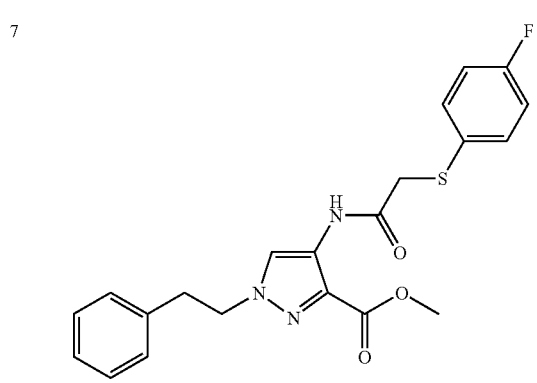
8
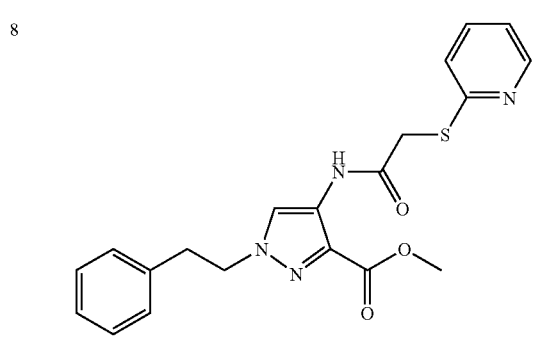
TABLE 1-continued
9
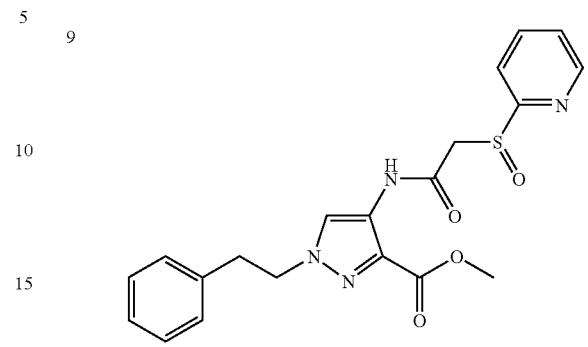
10
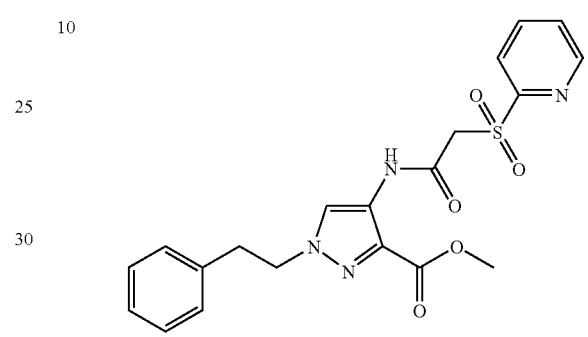
11
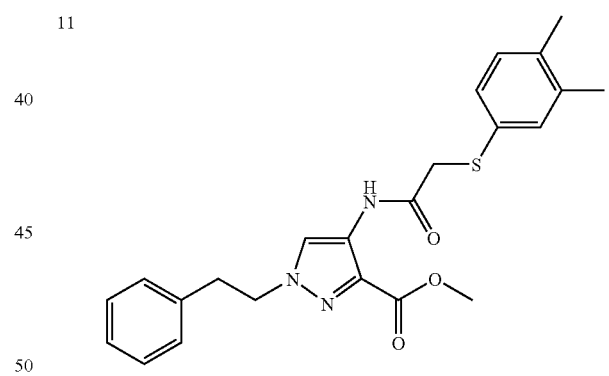
12
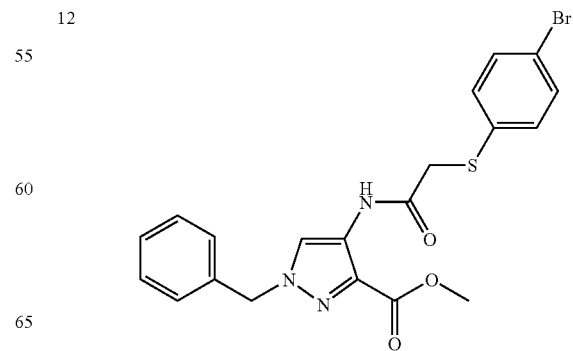

TABLE 1-continued
13
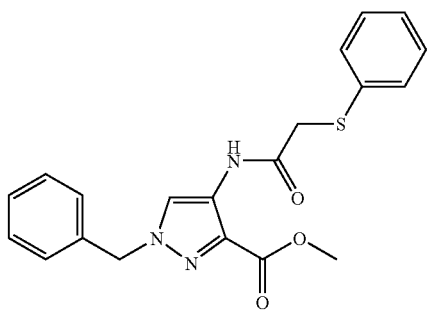
14
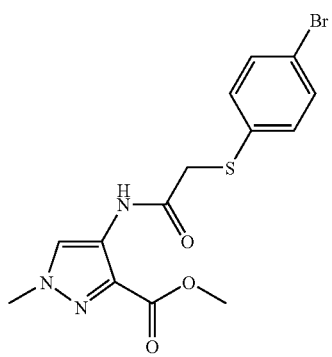
15
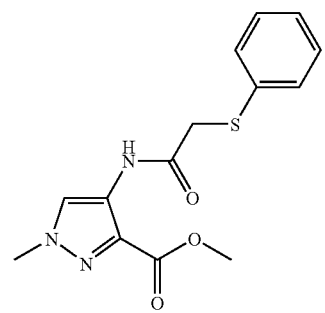
16
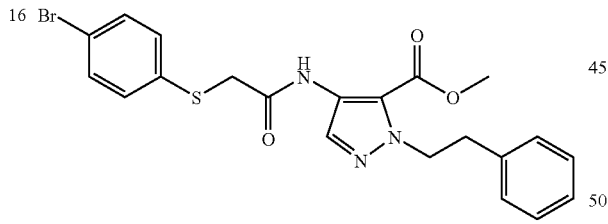
17
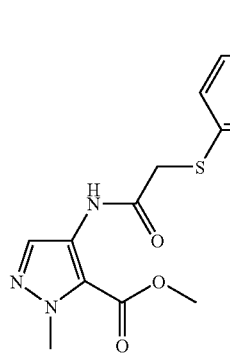
TABLE 1-continued
18
19
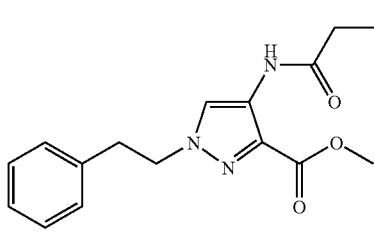
20
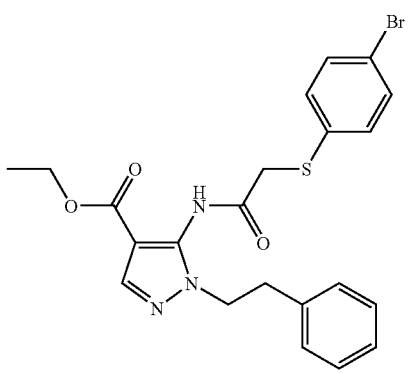
21
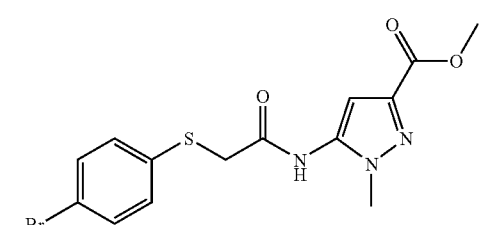
22
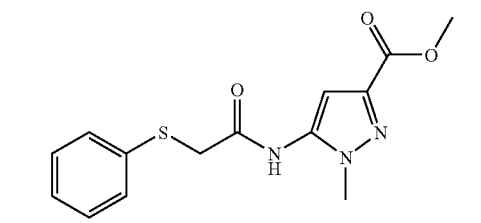

TABLE 1-continued
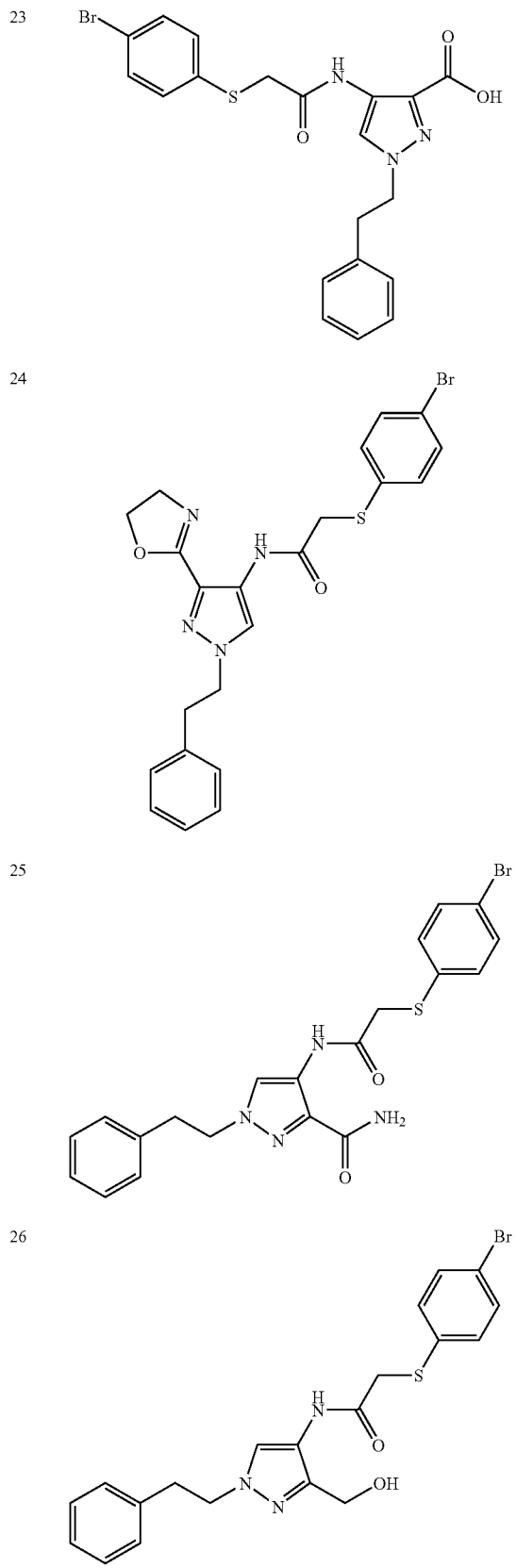
TABLE 1-continued
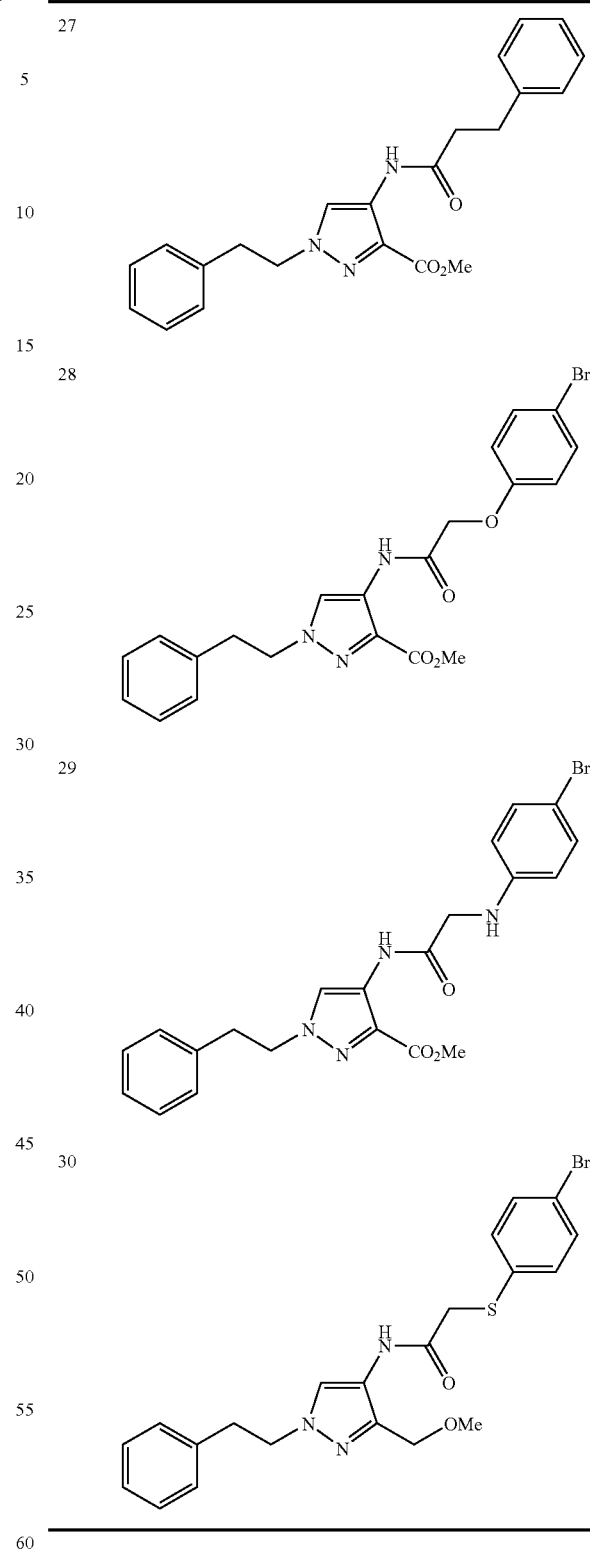
Also, the present invention provides a method for the preparation of aminopyrazole derivatives of Formula 1 above.
The aminopyrazole derivatives of the present invention, as represented by Formula 1 below, may be prepared by reacting aminopyrazole derivatives of Formula 2 with the compounds of Formula 3.

prepared by a conventional method, via alkylation, reduction and amide formation, as illustrated in the following Scheme 1.

Formula 2

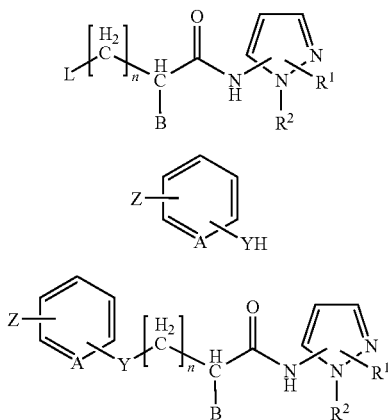

Formula 3

Formula 1 wherein
$R^1$, $R^2$, B, n, Y, Z and A are as defined in Formula 1, and L is a leaving group.

In Formula 1, when $R^1$ is ester, the aminopyrazole derivatives of Formula 1a can be produced through a nucleophilic substitution reaction by reacting the compound of Formula 2a having a leaving group L with the compound of Formula 3 as indicated below:

Formula 2a

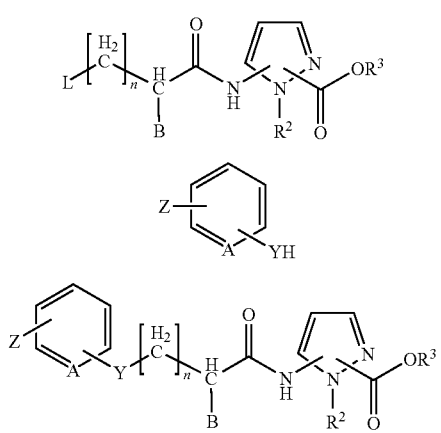

Formula 3

Formula 1a wherein
$R^2$, Z, n, A and B are as defined in Formula 1, Y is S, O or $NR^3R^4$, $R^3$ is H, or $C_1$-$C_2$ straight alkyl, and L as a leaving group is halide, mesylate or tosylate group.

In this reaction, an organic base such as pyridine, triethylamine, N,N-diisopropylethylamine, 1,8-diazabicyclo[5,4,0]-unde-7-cene (DBU), or NaOH, $Na_2CO_3$, $K_2CO_3$ or $Cs_2CO_3$ and the like may be used as a base in an equivalent amount or an excess.

For the reaction, ether-based solvents such as tetrahydrofuran, dioxane, dichloromethane and 1,2-dimethoxyethane, dimethylformamide (DMF), dimethylsulfoxide and the like may be used as a solvent alone or in combination. The reaction may be conducted at a temperature ranging from 0° C. to the boiling point of the solvent used.

Meanwhile, the compound of Formula 2aa (i.e., the compound having Br as L in Formula 2a) may be prepared from nitro-pyrazole-carboxylic acid alkyl ester of Formula 5 as a starting material, which is commercially available or may be Scheme 1

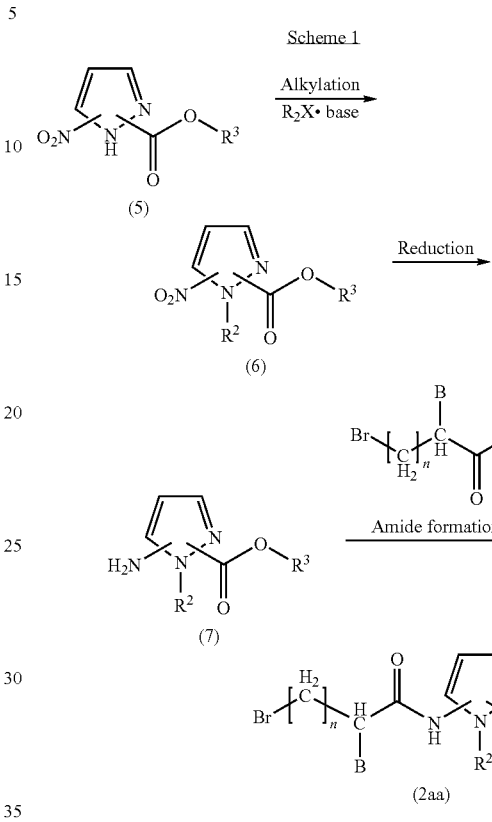

wherein
$R^2$, $R^3$, n and B are as defined in Formula 1a; D is OH, Br or Cl; and X is halogen.

In the alkylation of Scheme 1, the compound of Formula 6 may be prepared by reacting compound $R_2X$ having alkyl, phenethyl or benzyl and halogen with nitro-pyrazole-carboxylic acid alkyl ester of Formula 5 in the presence of a base. The base suitable for this reaction may be an equivalent or an excess amount of an inorganic base such as sodium hydride, potassium t-butoxide, sodium methoxide, $K_2CO_3$, NaOAc, KOAc, NaOH, KOH, $Na_2CO_3$, $BaCO_3$ and $Cs_2CO_3$. Further, the ether-based solvents such as tetrahydrofuran, dioxane, 1,2-dimethoxyethane, DMF, dimethylsulfoxide and the like may be used as a solvent alone or in combination. The reaction may be conducted at a temperature ranging from 0° C. to the boiling point of the solvent used.

In the reduction of Scheme 1, the compound of Formula 7 may be prepared by hydrogenating the compound of Formula 6 with hydrogen gas in the presence of a palladium catalyst (Pd/C) or Raney nickel, or by reacting it with hydrazine hydrates and Raney nickel, $SnCl_2$.HCl or Fe.HCl and the like in the alcoholic solvent such as methanol. At this step, the reducing agent may be used in an equivalent or an excess amount, and the reaction temperature may be from the room temperature to the boiling point of the solvent used.

In the amide formation of Scheme 1, when D is bromide (Br) or chloride (Cl), the amide compound of Formula 2aa may be prepared from the compound of Formula 7 in the presence of a base. The base and the reaction condition are the same as in the substitution reaction for the preparation of the compound of Formula 1a. When D is a hydroxyl group, the amide compound of Formula 2aa may be prepared by using a condensation agent such as 1,3-dicyclohexylcarbodiimide (DCC), 1,3-diisopropylcarbodiimide (DIC), 1-(3-dimethylaminopropyl)-3-ethylcarbodiimide (EDC) or 1,1-carbonyldiimidazole (CDI). For this reaction, dichloromethane, chloroform, tetrahydrofuran, DMF and the like may be used as a solvent, and the reaction temperature may be from the room temperature to the boiling point of the solvent used.

Meanwhile, the aminopyrazole derivatives of Formula 1a wherein n is 1 (i.e., the aminopyrazole derivatives of Formula 1aa) may be also prepared by conducting 1,4-addition reaction with the compound of Formula 4 having a double bond and an equivalent or an excess amount of the compound of Formula 3. The base and the reaction conditions are the same as in the preparation of the compound of Formula 1a.

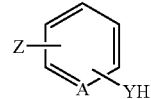

Formula 3

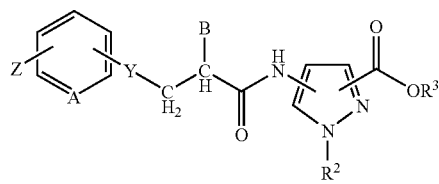

Formula 1aa

Formula 4

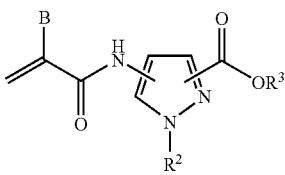

wherein
$R^2$, $R^3$, Y, Z, A and B are as defined in Formula 1a.

The compound of Formula 4 may be prepared by reacting the compound of Formula 2a where in n is 1 with an equivalent or an excess amount of a base to remove leaving group L from the compound of Formula 2a, or via amide formation reaction of the compound of Formula 7 as illustrated in Scheme 1 above and acryloyl halide.

In addition, various aminopyrazole derivatives may be prepared by modifying the ester group in the aminopyrazole derivatives of Formula 1a, as depicted in Scheme 2 below.

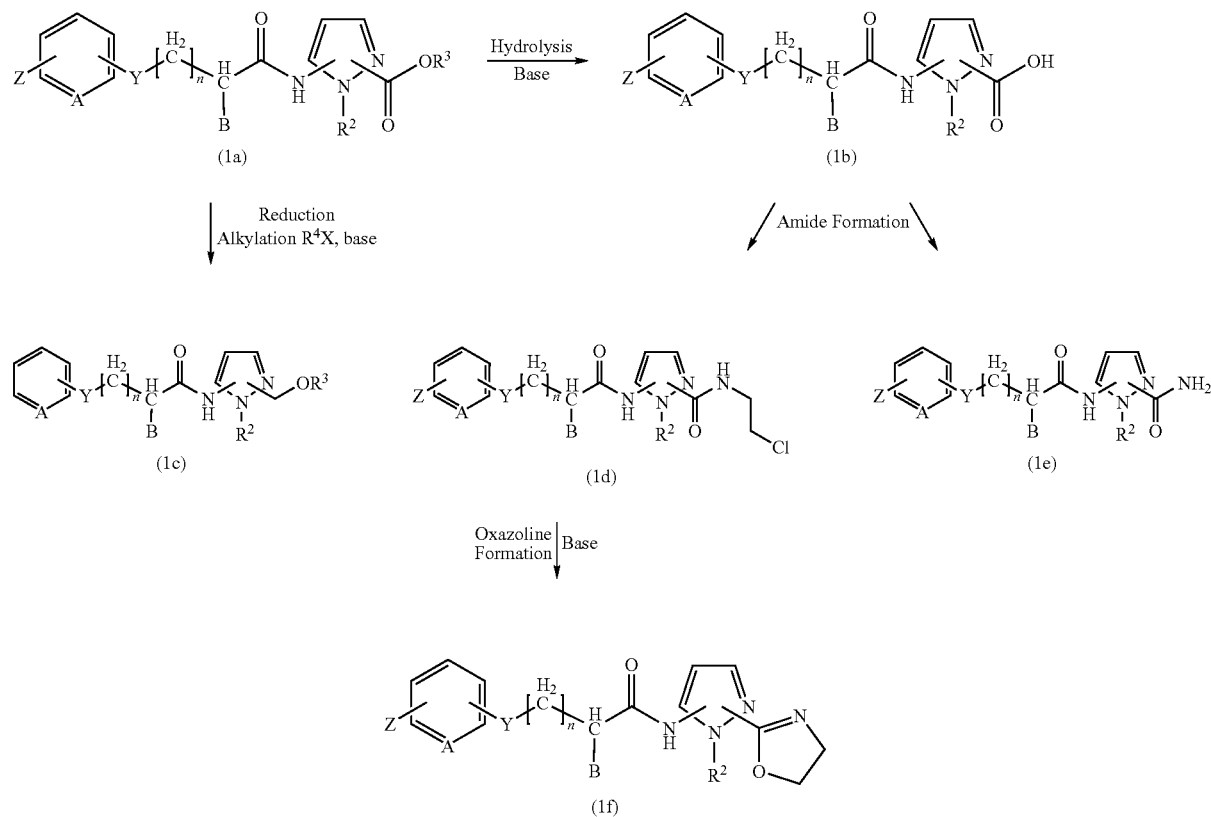

Scheme 2 wherein $R^2$, $R^3$, Y, Z, A and B are as defined in Formula 1a; $R^4$ is $C_1$-$C_4$ straight or branched alkyl group; and X is halogen.

As illustrated in Scheme 2 above, the carboxylic acid derivatives of Formula 1b may be prepared by hydrolyzing the ester group of the aminopyrazole derivatives of Formula 1a with a base. An alcoholic solvent such as methanol or an ether-based solvent such as tetrahydrofuran or dioxane may be used as the reaction solvent alone or in combination. As the base, sodium hydroxide or potassium hydroxide may be used in 1 to 5 equivalents. The reaction temperature may be from 0° C. to the boiling point of the solvent used.

In addition, as illustrated in Scheme 2 above, the reduction reaction may be conducted by reducing the ester group of the aminopyrazole derivatives of Formula 1a to alcohol group, and then reducing the alcohol compound with a halogen compound having $C_1$-$C_4$ straight or branched chain alkyl group to produce the aminopyrazole derivatives of Formula 1c. Preferably, sodium borohydride in the alcoholic solvent such as methanol or lithium borohydride in the tetrahydrofuran as a solvent can be used to provide alcohol derivatives. Such reducing agents may be used in an equivalent or an excess amount, and the reaction temperature may be from 0° C. to the boiling point of the solvent used.

In the alkylation, inorganic bases such as sodium hydride, potassium t-butoxide, sodium methoxide, $K_2CO_3$, NaOAc, KOAc, NaOH, KOH, $Na_2CO_3$, $BaCO_3$, $Cs_2CO_3$ and the like may be used in an equivalent or an excess amount. Ether-based solvents such as tetrahydrofuran, dioxane and 1,2-dimethoxyethane, DMF or dimethylsulfoxide may be used as the reaction solvents alone or in combination. The reaction may be conducted at a temperature ranging from 0° C. to the boiling point of the solvent used.

In the amide formation reaction of Scheme 2 above, the aminopyrazole derivatives of Formula 1d may be prepared by reacting the carboxylic acid derivatives of Formula 1b with an condensing agent such as DCC, DIC, EDC and CDI, and subsequently reacting the resulting 2-chloroethylamine hydrochloride under an excess amount of a base. Further, the aminopyrazole derivatives of Formula 1e may be prepared by reacting the compound of Formula 1b with an excess amount of aqueous ammonia. Ether-based solvents such as tetrahydrofuran, dioxane, dichloromethane and 1,2-dimethoxyethane, DMF or dimethylsulfoxide may be used as the reaction solvents alone or in combination. The base may be used in an equivalent or an excess amount, and the reaction temperature may be from 0° C. to the boiling point of the solvent used.

Also, in Scheme 2, the aminopyrazole derivatives of Formula 1d may be subjected to an oxazolidine heterocyclization reaction in the presence of a base to produce the aminopyrazole derivatives of Formula 1f. As the base, DBU may be used, and tetrahydrofuran, benzene or toluene may be used as a solvent. The reaction temperature is allowed ranging from the room temperature to the boiling point of the solvent used.

Meanwhile, the present invention provides a composition for the prevention or treatment of ischemic diseases, and for the protection of organs, containing the aminopyrazole derivatives or the pharmaceutically acceptable salts thereof.

The aminopyrazole derivatives of the present invention, the pharmaceutically acceptable salts thereof, and the pharmaceutical composition containing the same may be clinically administered in oral or non-oral forms. It is usually formulated in combination with a diluent or excipient such as a filler, a thickening agent, a binder, a wetting agent, a disintegrant or a surfactant, etc.

Solid agents intended for oral administration may be prepared by mixing at least one aminopyrazole derivatives of the present invention with at least one excipient such as starch, calcium carbonate, sucrose, lactose or gelatine. Besides, a lubricant such as magnesium stearate, talc, and the like may be added, as well.

Liquid agents intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be used in the liquid agents for the oral administration of the compound of the present invention.

Also, the compound of the present invention may be administered via a non-oral route. For this, sterile aqueous solutions, non-aqueous solvents, suspensions, emulsions, lyopphilics, suppositories, and the like may be used. Injectable vegetable oil such as propylene glycol, polyethylene glycol or an olive oil and ester such as ethyl olate may be suitable for non-aqueous solvents and suspensions. The basic materials of suppositories include witepsol, macrogol, tween 61, cacao paper, laurin paper, glycerol and gelatine.

Depending on the conditions of patients, including age, body weight, sex, administration route, health state, and disease severity, the administration dose of the aminopyrazole derivatives of the present invention, the pharmaceutically acceptable salts thereof, and the pharmaceutical composition containing the same to humans may vary. Typically, the compound of the present invention is administered at a dose from 0.1 to 1,000 mg a day for an adult weighing 70 kg, and preferably at a dose from 1 to 500 mg a day. The compound may be administered in a single dose or in divided doses per day.

The present invention is further described particularly by the following examples which are set forth to illustrate, but are not to be construed as the limit of the present invention.

In the present invention, molecular structures of compounds were confirmed using infrared spectroscopy, NMR spectroscopy, mass spectroscopy, liquid chromatography, X-ray crystallography, optical rotation spectroscopy, or elemental analysis for comparing calculated values of representative elements with experimentally observed values thereof.

Preparative Example 1

4-nitro-1-phenethyl-1H-pyrazole-3-carboxylic acid methyl ester 430 mg (2.5 mM) of 4-nitro-1H-pyrazole-3-carboxylic acid methyl ester was dissolved in 4 ml of N,N-dimethylformamide, to which 0.41 ml (3 mM) of (2-bromoethyl)benzene and 1.6 g (5.0 mM) of cesium carbonate were added dropwise, and the mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=5:1), to obtain 506 mg (65.5%) of the title compound and 218 mg (31.2%) of the compound of Preparative Example 10.

$^1$H NMR (300 MHz, $CDCl_3$) δ 3.20 (t, J=7.0 Hz, 2H), 3.99 (s, 3H), 4.39 (t, J=7.0 Hz, 2H), 7.03-7.08 (m, 2H), 7.03-7.08 (m, 3H), 7.78 (s, 1H).

Preparative Example 2

4-amino-1-phenethyl-1H-pyrazole-3-carboxylic acid methyl ester 27.9 g (101.1 mM) of the compound obtained in Preparative Example 1 was dissolved in 150 ml of methanol, to which 2.8 g of 10% palladium/charcoal was added dropwise, and the resulting mixture was stirred under hydrogen pressure of 40 atm for 30 minutes. After the reaction was terminated, the resulting reaction solution was filtered through cellite, and distilled under reduced pressure, to obtain 23.3 g (94.2%) of the title compound.

$^1$H NMR (300 MHz, DMSO) δ 2.92 (t, 2H), 3.68 (s, 3H), 4.16 (t, 2H), 6.99-7.16 (m, 6H).

Preparative Example 3

4-(2-bromoacetylamino)-1-phenethyl-1H-pyrazole-3-carboxylic acid methyl ester 23.3 g (95.1 mM) of the compound obtained in Preparative Example 2 was dissolved in 150 ml of tetrahydrofuran, to which 9.1 ml (114.0 mM, 1.2 eq) of bromo acetylbromide and 20.0 ml (142.7 mM, 1.5 eq) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 28.2 g (81.3%) of the title compound.

$^1$H NMR (300 MHz, CDCl$_3$) δ 3.17 (t, 2H), 4.01 (s, 5H), 4.36 (t, 2H), 7.12 (d, 2H), 7.15 (m, 3H), 8.10 (s, 1H), 9.95 (br, NH).

Mass: 366 (M$^+$)

Preparative Example 4

4-nitro-1-benzyl-1H-pyrazole-3-carboxylic acid methyl ester 82 mg (0.48 mM) of 4-nitro-1H-pyrazole-3-carboxylic acid methyl ester was dissolved in 2 ml of N,N-dimethylformamide, to which 63 μl (0.53 mM) of (2-bromomethyl)benzene and 313 mg (0.96 mM) of cesium carbonate were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=6:1), to obtain 81 mg (65%) of the title compound and 20 mg (17%) of 2-benzyl compound.

$^1$H NMR (300 MHz, CDCl$_3$) δ 4.00 (s, 3H), 5.34 (s, 2H), 7.30 (m, 2H), 7.41 (m, 3H), 8.00 (s, 1H).

Mass: 261 (M$^+$)

Preparative Example 5

4-amino-1-benzyl-1H-pyrazole-3-carboxylic acid methyl ester 335 mg (1.28 mM) of the compound obtained in Preparative Example 4 was dissolved in 5 ml of methanol, to which Raney nickel is added, and the resulting mixture was stirred under hydrogen pressure of 30 atm for 2.5 hours. After the reaction was terminated, the resulting reaction solution was filtered through cellite, and distilled under reduced pressure, to obtain 294 mg (99%) of the title compound.

$^1$H NMR (300 MHz, CDCl$_3$) δ 3.85 (s, 3H), 5.21 (s, 2H), 7.15 (s, 3H), 7.26 (s, 3H).

Preparative Example 6

4-(2-bromoacetylamino)-1-benzyl-1H-pyrazole-3-carboxylic acid methyl ester 130 mg (0.56 mM) of the compound obtained in Preparative Example 5 was dissolved in 3 ml of tetrahydrofuran, to which 59 μl (0.67 mM) of bromo acetylbromide and 0.12 ml (0.84 mM) of triethylamine were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 140 mg (71%) of the title compound:

$^1$H NMR (300 MHz, CDCl$_3$) δ 4.00 (s, 5H), 5.30 (s, 2H), 7.25 (m, 2H), 7.32 (m, 3H), 8.17 (s, 1H), 9.97 (br, NH).

Mass: 351 (Br79$^+$), 353 (Br81)

Preparative Example 7

4-nitro-1-methyl-1H-pyrazole-3-carboxylic acid methyl ester 340 mg (1.99 mM) of 4-nitro-1H-pyrazole-3-carboxylic acid methyl ester was dissolved in 4 ml of N,N-dimethylformamide, to which 0.33 ml (2.19 mM) of iodomethane and 1.3 g (3.98 mM) of cesium carbonate were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 195 mg (53%) of the title compound and 110 mg (30%) of the compound of Preparative Example 13.

$^1$H NMR (300 MHz, CDCl$_3$) δ 4.00 (s, 3H), 4.02 (s, 3H), 8.15 (s, 1H).

Mass: 185 (M$^+$)

Preparative Example 8

4-amino-1-methyl-1H-pyrazole-3-carboxylic acid methyl ester 240 mg (1.30 mM) of the compound obtained in Preparative Example 7 was dissolved in 5 ml of methanol, to which 24 mg of 10% palladium/charcoal was added dropwise, and the resulting mixture was stirred under hydrogen pressure of 40 atm for 30 minutes. After the reaction was terminated, the resulting reaction solution was filtered through cellite, and distilled under reduced pressure, to obtain 191 mg (95%) of the title compound.

$^1$H NMR (300 MHz, CDCl$_3$) δ 3.86 (s, 3H), 3.92 (s, 3H), 6.91 (s, 1H).

Mass: 155 (M$^+$)

Preparative Example 9

4-(2-bromoacetylamino)-1-methyl-1H-pyrazole-3-carboxylic acid methyl ester 160 mg (1.03 mM) of the compound obtained in Preparative Example 8 was dissolved in 3 ml of tetrahydrofuran, to which 0.11 ml (1.24 mM) of bromo acetylbromide and 0.22 ml (1.55 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 100 mg (69%) of the title compound.

$^1$H NMR (300 MHz, CDCl$_3$) δ 3.79 (s, 3H), 3.99 (s, 3H), 4.03 (s, 2H), 8.20 (s, 1H), 9.95 (br, NH).

Mass: 275 (Br79$^+$), 277 (Br81)

Preparative Example 10

4-nitro-2-phenethyl-2H-pyrazole-3-carboxylic acid methyl ester 430 mg (2.5 mM) of 4-nitro-1H-pyrazole-3-carboxylic acid methyl ester was dissolved in 4 ml of N,N-dimethylformamide, to which 0.41 ml (3 mM) of (2-bromoethyl)benzene and 1.6 g (5.0 mM) of cesium carbonate were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=5:1), to obtain 218 mg (31.2%) of the title compound and 506 mg (65.5%) of the compound of Preparative Example 1.

$^1$H NMR (300 MHz, CDCl$_3$) δ 3.13 (t, J=7.1 Hz, 2H), 3.82 (s, 3H), 4.52 (t, J=7.1 Hz, 2H), 7.00-7.05 (m, 2H), 7.22-7.64 (m, 3H), 8.05 (s, 1H).

Preparative Example 11

4-amino-2-phenethyl-2H-pyrazole-3-carboxylic acid methyl ester 51 mg (0.19 mM) of the compound obtained in Preparative Example 10 was dissolved in 1 ml of methanol, to which 5 mg of 10% palladium/charcoal was added, and the resulting mixture was stirred under hydrogen pressure of 40 atm for 5 hours. After the reaction was terminated, the resulting reaction solution was filtered through cellite, and distilled under reduced pressure, to obtain 36 mg (80.0%) of the title compound.

$^1$H NMR (300 MHz, CDCl$_3$) δ 3.05 (t, J=6.9 Hz, 2H), 3.89 (s, 3H), 4.10 (brs, 2H), 4.61 (t, J=6.9 Hz, 2H), 7.10 (s, 1H), 7.18-7.31 (m, 5H).

Preparative Example 12

4-(2-bromoacetylamino)-2-phenethyl-2H-pyrazole-3-carboxylic acid methyl ester 82 mg (0.3 mM) of the compound obtained in Preparative Example 11 was dissolved in 1 ml of tetrahydrofuran, to which 0.04 ml (0.4 mM, 1.2 eq) of bromo acetylbromide and 0.07 ml (0.5 mM, 1.5 eq) of triethylamine were added dropwise, and the resulting mixture was stirred under a nitrogen atmosphere for 5 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 88 mg (73.3%) of the title compound.

$^1$H NMR (300 MHz, CDCl$_3$) δ 3.09 (t, J=7.2 Hz, 2H), 3.95 (s, 3H), 4.04 (s, 2H), 4.72 (t, J=7.2 Hz, 2H), 7.13-7.31 (m, 5H), 8.31 (s, 1H), 9.74 (brs, 1H).

Preparative Example 13

4-nitro-2-methyl-2H-pyrazole-3-carboxylic acid methyl ester 340 mg (1.99 mM) of 4-nitro-1H-pyrazole-3-carboxylic acid methyl ester was dissolved in 4 ml of N,N-dimethylformamide, to which 0.33 ml (2.19 mM) of iodomethane and 1.3 g (3.98 mM) of cesium carbonate were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 110 mg (30%) of the title compound and 195 mg (53%) of the compound of Preparative Example 7.

$^1$H NMR (300 MHz, CDCl$_3$) δ 4.03 (s, 3H), 4.04 (s, 3H), 8.03 (s, 1H).

Preparative Example 14

4-amino-2-methyl-2H-pyrazole-3-carboxylic acid methyl ester 127 mg (0.69 mM) of the compound obtained in Preparative Example 13 was dissolved in 3 ml of methanol, to which 10% palladium/charcoal was added, and the resulting mixture was stirred under hydrogen pressure of 40 atm for 2 hours. After the reaction was terminated, the resulting reaction solution was filtered through cellite, and distilled under reduced pressure, to obtain 43 mg (41%) of the title compound.

$^1$H NMR (300 MHz, CDCl$_3$) δ 3.92 (s, 3H), 4.04 (s, 3H), 4.09 (br, NH$_2$), 7.08 (s, 1H).

Mass: 155 (M$^+$)

Preparative Example 15

4-(2-bromoacetylamino)-2-methyl-2H-pyrazole-3-carboxylic acid methyl ester 42 mg (0.27 mM) of the compound obtained in Preparative Example 14 was dissolved in 1 ml of tetrahydrofuran, to which 28 μl (0.32 mM) of bromo acetylbromide and 57 μl (0.41 mM) of triethylamine were added dropwise, and the resulting mixture was stirred under a nitrogen atmosphere for 1 hours. The solvent was distilled off under reduced pressure, and the resultant was extracted with ethyl acetate and brine. The organic solvent layer was dried over anhydrous sodium sulfate, filtered, and then distilled under reduced pressure.

The resulting impure compound was purified by column chromatography (hexane:ethyl acetate=2:1), to obtain 36 mg (85%) of the title compound.

$^1$H NMR (300 MHz, CDCl$_3$) δ 4.03 (s, 3H), 4.11 (s, 3H), 4.05 (s, 2H), 8.37 (s, 1H), 10.01 (br, NH).

Preparative Example 16

4-(3-bromopropionylamino)-1-phenethyl-1H-pyrazole-3-carboxylic acid methyl ester 3-bromopropionic acid was dissolved in 50 ml of tetrahydrofuran, to which 1.64 ml (10.6 mM) of diisopropylcarbodiimide was added, and the resulting mixture was stirred for 30 minutes. Subsequently, 1.3 g (5.3 mM) of the compound obtained in Preparative Example 2 was added dropwise thereto, and the resulting mixture was stirred under a nitrogen atmosphere for 3 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 1.95 g (96%) of the title compound.

$^1$H NMR (300 MHz, CDCl$_3$) δ 3.03 (t, 2H), 3.70 (t, 2H), 3.98 (s, 3H), 4.39 (t, 2H), 7.15 (d, 2H), 7.21-7.32 (m, 3H), 8.16 (s, 1H), 9.09 (br, NH).

Preparative Example 17

4-acryloylamino-1-phenethyl-1H-pyrazole-3-carboxylic acid methyl ester 1.95 g (5.13 mM) of the compound obtained in Preparative Example 16 was dissolved in 15 ml of dichloromethane, to which 1.08 ml (12.82 mM, 2.5 eq) of triethylamine was added dropwise, and the resulting mixture was stirred under a nitrogen atmosphere for 5 hours. The solvent was distilled off under reduced pressure, and the resultant was extracted with ethyl acetate and brine. The organic solvent layer was dried over anhydrous sodium sulfate, filtered, and distilled under reduced pressure, to obtain 1.12 g (72%) of the title compound.

$^1$H NMR (300 MHz, CDCl$_3$) δ 3.22 (t, 2H), 3.99 (s, 3H), 4.40 (t, 2H), 5.80 (t, 1H), 6.23-6.43 (m, 2H), 7.15 (d, 2H), 7.20-7.32 (m, 3H), 8.20 (s, 1H), 9.14 (br, NH).

Preparative Example 18

5-amino-1-phenethyl-1H-pyrazole-3-carboxylic acid ethyl ester 200 mg (1.3 mM) of 3-amino-1H-pyrazole-3-carboxylic acid ethyl ester was dissolved in 3 ml of N,N-dimethylformamide, to which 0.21 ml (1.6 mM, 1.2 eq) of 2-bromoethylbenzene and 840 mg (2.6 mM, 2.0 eq) of cesium carbonate were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=4:1), to obtain 117 mg (35.0%) of the title compound.

$^1$H NMR (300 MHz, CDCl$_3$) δ 1.30 (t, J=6.9 Hz, 3H), 3.14 (t, J=7.2 Hz, 2H), 4.10 (t, J=6.9 Hz, 2H), 4.23 (t, J=7.2 Hz, 2H), 4.64 (brs, 2H), 7.08-7.11 (m, 2H), 7.21-7.32 (m, 3H), 7.38 (s, 1H).

Preparative Example 19

5-(2-bromo-3-acetylamino)-1-phenethyl-1H-pyrazole-4-carboxylic acid ethyl ester 80 mg (0.3 mM) of the compound obtained in Preparative Example 18 was dissolved in 2 ml of tetrahydrofuran, to which 0.03 ml (0.4 mM, 1.3 eq) of bromo acetylbromide and 0.06 ml (0.4 mM, 1.3 eq) of triethylamine were added dropwise, and the resulting mixture was stirred under a nitrogen atmosphere for 2 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 110 mg (94.0%) of the title compound.

$^1$H NMR (300 MHz, CDCl$_3$) δ 1.28-1.36 (m, 3H), 3.19 (t, J=7.2 Hz, 2H), 4.07 (s, 2H), 4.25-4.36 (m, 4H), 7.09 (d, J=6.6 Hz, 2H), 7.21-7.32 (m, 3H), 7.50 (s, 1H), 10.12 (brs, 1H).

Preparative Example 20

4-(2-bromo-2-phenyl-acetylamino)-1-phenethyl-1H-pyrazole-3-carboxylic acid methyl ester 264 mg (1.23 mM) of 2-bromophenylacetic acid was dissolved in 4 ml of dichloromethane, to which 0.19 ml (1.23 mM) of diisopropylcarbodiimide was added, and the resulting mixture was stirred for 30 minutes. Subsequently, 200 mg (0.82 mM) of the compound obtained in Preparative Example 2 was added thereto, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 280 mg (77%) of the title compound.

$^1$H NMR (300 MHz, CDCl$_3$) δ 3.15 (t, 2H), 4.00 (s, 3H), 4.34 (t, 2H), 5.54 (s, 1H), 7.12 (d, 2H), 7.23-7.31 (m, 3H), 7.35 (m, 3H), 7.50 (dd, 2H), 8.12 (s, 1H), 10.08 (s, NH).

Mass (m/e, M$^+$): 441, 443

Preparative Example 21

1-methyl-5-nitro-1H-pyrazole-3-carboxylic acid methyl ester 500 mg (2.93 mM) of 5-nitro-1H-pyrazole-3-carboxylic acid methyl ester was dissolved in 5 ml of N,N-dimethylformamide, to which 810 mg (5.86 mM, eq) of potassium carbonate was added. Subsequently, 0.49 ml (3.22 mM) of iodomethane was added dropwise thereto at 0° C., and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=10:1), to obtain 314 mg (56%) of the title compound.

$^1$H NMR (300 MHz, CDCl$_3$) δ 7.40 (s, 1H, ArH), 4.29 (s, 3H, OCH$_3$), 3.96 (s, 3H, N—CH$_3$).

Mass (m/e, M$^+$): 185

Preparative Example 22

5-amino-1-methyl-1H-pyrazole-3-carboxylic acid methyl ester 136 mg (0.74 mM) of the compound obtained in Preparative Example 21 was dissolved in 2 ml of methanol, to which 14 mg of 10% palladium/charcoal was added dropwise, and the resulting mixture was stirred under hydrogen pressure of 50 atm for 1 hour. After the reaction was terminated, the resulting reaction solution was filtered through cellite, and distilled under reduced pressure, to obtain 94 mg (82%) of the title compound.

$^1$H NMR (300 MHz, CDCl$_3$) δ 6.12 (s, 1H, ArH), 3.99 (s, 3H, OCH$_3$), 3.84 (s, 3H, N—CH$_3$), 3.72 (brs, 2H, NH$_2$).

Preparative Example 23

5-(2-bromo-acetylamino)-1-methyl-1H-pyrazole-3-carboxylic acid methyl ester 200 mg (1.29 mM) of the compound obtained in Preparative Example 22 was dissolved in 3 ml of tetrahydrofuran, to which 0.13 ml (1.55 mM) of bromo acetylbromide and 0.27 ml (1.94 mM) of triethylamine were added dropwise, and the resulting mixture was stirred under a nitrogen atmosphere for 30 minutes. The solvent was distilled off under reduced pressure, AND the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 349 mg (98%) of the title compound.

$^1$H NMR (300 MHz, CDCl$_3$) δ 8.67 (brs, 1H, N—H), 7.22 (s, 1H, ArH), 4.10 (s, 3H, OCH$_3$), 4.02 (s, 2H, COCH$_2$), 3.89 (s, 3H, N—CH$_3$).

Preparative Example 24

4-nitro-3-hydroxymethyl-1-phenethyl-1H-pyrazole 495 mg (1.8 mM) of 4-nitro-1-phenethyl-1H-pyrazole-3-carboxylic acid ethyl ester was dissolved in 5 ml of methyl alcohol, to which 680 mg (18 mM, 13 eq) of sodium borohydride was added dropwise at 0° C., and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 295 mg (66.4%) of the title compound.

$^1$H NMR (300 MHz, CDCl$_3$) δ 2.89 (brs, 1H), 3.19 (t, J=7.8 Hz, 2H), 4.33 (t, J=7.8 Hz, 2H), 4.92 (s, 2H), 7.06-7.09 (m, 2H), 7.28-7.34 (m, 3H), 7.84 (s, 1H).

Preparative Example 25

4-nitro-3-methoxymethyl-1-phenethyl-1H-pyrazole 1.3 g (5.3 mM) of the compound obtained in Preparative Example 24 was dissolved in 10 ml of N,N-dimethylformamide, to which 253 mg (6.3 mM, 1.2 eq) of sodium hydride and 0.43 ml (6.9 mM, 1.5 eq) of iodomethane were added at 0° C., and the resulting mixture was stirred at room temperature under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 780 mg (56.9%) of the title compound.

$^1$H NMR (300 MHz, CDCl$_3$) δ 3.19 (t, J=7.8 Hz, 2H), 3.52 (s, 3H), 4.36 (t, J=7.8 Hz, 2H), 4.81 (s, 2H), 7.07 (dd, J=7.8, 1.8 Hz, 2H), 7.25-7.33 (m, 3H), 7.84 (s, 1H).

Preparative Example 26

4-nitro-3-methoxymethyl-1-phenethyl-1H-pyrazole 680 mg (2.6 mM) of the compound obtained in Preparative Example 25 was dissolved in 7 ml of methyl alcohol, to which 7.23 ml (2.6 mM, 1 eq) of copper acetate and 1180 mg (31.3 mM, 12 eq) of sodium borohydride were added at 0° C., and the resulting mixture was stirred under a nitrogen atmosphere for 10 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:2), to obtain 456 mg (75.9%) of the title compound.

$^1$H NMR (300 MHz, CDCl$_3$) δ 2.89 (brs, 2H), 3.11 (t, J=7.8 Hz, 2H), 3.37 (s, 3H), 4.17 (t, J=7.8 Hz, 2H), 4.50 (s, 2H), 6.79 (s, 1H), 7.10 (dd, J=7.8, 1.3 Hz, 2H), 7.18-7.30 (m, 3H).

Preparative Example 27

4-(2-bromo-acetylamino)-3-methoxymethyl-1-phenethyl-1H-pyrazole 40 mg (0.17 mM) of the compound obtained in Preparative Example 26 was dissolved in 2 ml of tetrahydrofuran, to which 0.02 ml (0.23 mM, 1.3 eq) of bromo acetylbromide and 0.04 ml (0.26 mM, 1.5 eq) of triethylamine were added dropwise, and the resulting mixture was stirred under a nitrogen atmosphere for 2 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 52 mg (86.7%) of the title compound.

$^1$H NMR (300 MHz, CDCl$_3$) δ 3.13 (t, J=7.8 Hz, 2H), 3.47 (s, 3H), 3.99 (s, 2H), 4.25 (t, J=7.8 Hz, 2H), 4.68 (s, 2H), 7.13 (d, J=7.0 Hz, 2H), 7.19-7.31 (m, 3H), 7.96 (s, 1H), 9.07 (brs, 1H).

Example 1

Preparation of 4-[2-(4-bromo-phenylsulfanyl)-acetylamino]-1-phenethyl-1H-pyrazole-3-carboxylic acid methyl ester 1.67 g (4.56 mM) of the compound obtained in Preparative Example 3 was dissolved in 20 ml of tetrahydrofuran, to which 1.03 g (5.47 mM) of 4-bromobenzenethiol and 0.82 ml (5.93 mM) of triethylamine were added dropwise, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 2.04 g (94%) of the title compound.

$^1$H NMR (300 MHz, CDCl$_3$) δ 3.18 (t, J=7.8 Hz, 2H), 3.74 (s, 2H), 3.99 (s, 3H), 4.36 (t, J=7.8 Hz, 2H), 7.12-7.15 (m, 2H), 7.24-7.31 (m, 5H), 7.39-7.43 (m, 2H), 8.10 (s, 1H), 10.14 (brs, 1H).

Mass (m/e, M$^+$): 475, 473

Example 2

Preparation of 4-[2-(phenylsulfanyl)-acetylamino]-1-phenethyl-1H-pyrazole-3-carboxylic acid methyl ester 1.0 g (2.73 mM) of the compound obtained in Preparative Example 3 was dissolved in 10 ml of tetrahydrofuran, to which 0.34 ml (3.28 mM) of benzenethiol and 0.49 ml (3.28 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 971 mg (90%) of the title compound.

$^1$H NMR (300 MHz, CDCl$_3$) δ 3.15 (t, 2H), 3.73 (s, 2H), 3.98 (s, 3H), 4.32 (t, 2H), 7.12 (d, 2H), 7.19 (m, 6H), 7.39 (d, 2H), 8.12 (s, 1H), 10.23 (br, NH).

Mass (m/e, M$^+$): 395

Example 3

Preparation of 4-[2-(3-methoxy-phenylsulfanyl)-acetylamino]-1-phenethyl-1H-pyrazole-3-carboxylic acid methyl ester 80 mg (0.2 mM) of the compound obtained in Preparative Example 3 was dissolved in 2 ml of tetrahydrofuran, to which 0.04 ml (0.3 mM, 1.5 eq) of 3-methoxybenzenethiol and 0.05 ml (0.3 mM, 1.5 eq) of triethylamine were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 90 mg (97.8%) of the title compound.

$^1$H NMR (300 MHz, CDCl$_3$) δ 3.17 (t, J=7.8 Hz, 2H), 3.75-3.76 (m, 5H), 3.96 (s, 3H), 3.99 (s, 2H), 4.34 (t, J=7.8 Hz, 2H), 6.74 (dt, J=8.4, 1.2 Hz, 1H), 6.97 (d, J=6.6 Hz 2H), 7.11-7.25 (m, 6H), 8.12 (s, 1H), 10.21 (brs, 1H).

Mass (m/e, M$^+$): 425, 394, 375, 321

Example 4

Preparation of 4-[2-(4-nitro-phenylsulfanyl)-acetylamino]-1-phenethyl-1H-pyrazole-3-carboxylic acid methyl ester 148 mg (0.4 mM) of the compound obtained in Preparative Example 3 was dissolved in 3 ml of tetrahydrofuran, to which 87 mg (0.6 mM, 1.5 eq) of 4-nitrothiophenol and 0.08 ml (0.6 mM, 1.5 eq) of triethylamine were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 51 mg (26.4%) of the title compound.

$^1$H NMR (300 MHz, CDCl$_3$) δ 3.17 (t, J=7.8 Hz, 2H), 3.88 (s, 3H), 3.95 (s, 2H), 4.36 (t, J=7.8 Hz, 2H), 7.12 (d, J=6.6 Hz, 2H), 7.23-7.28 (m, 3H), 7.43-7.46 (m, 2H), 8.09-8.16 (m, 3H), 10.02 (brs, 1H).

Mass (m/e, M$^+$): 440, 410, 366, 336, 317

Example 5

Preparation of 4-[2-(2-amino-phenylsulfanyl)-acetylamino]-1-phenethyl-1H-pyrazole-3-carboxylic acid methyl ester 163 mg (0.45 mM) of the compound obtained in Preparative Example 3 was dissolved in 4 ml of tetrahydrofuran, to which 0.07 ml (0.6 mM, 1.5 eq) of 2-aminothiophenol and 0.08 ml (0.6 mM, 1.5 eq) of triethylamine were added dropwise, and the resulting mixture was stirred under a nitrogen atmosphere for 15 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 168 mg (92.3%) of the title compound.

$^1$H NMR (300 MHz, CDCl$_3$) δ 3.18 (t, J=7.8 Hz, 2H), 3.60 (s, 2H), 4.00 (s, 3H), 4.32-4.38 (m, 4H), 6.61-6.71 (m, 2H), 7.08-7.14 (m, 3H), 7.25-7.29 (m, 3H), 7.44 (dd, J=7.5, 1.2 Hz, 1H), 8.10 (s, 1H), 9.96 (brs, 1H).

Mass (m/e, M$^+$): 410, 377, 335, 245

Example 6

Preparation of 4-[2-(4-methyl-phenylsulfanyl)-acetylamino]-1-phenethyl-1H-pyrazole-3-carboxylic acid methyl ester 80 mg (0.2 mM) of the compound obtained in Preparative Example 3 was dissolved in 2 ml of tetrahydrofuran, to which 38 mg (0.3 mM, 1.5 eq) of 4-methylbenzenethiol and 0.05 ml (0.3 mM, 1.5 eq) of triethylamine were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 87 mg (97.8%) of the title compound.

$^1$H NMR (300 MHz, CDCl$_3$) δ 3.17 (t, J=7.8 Hz, 2H), 3.71 (s, 2H), 4.00 (s, 3H), 4.34 (t, J=7.8 Hz, 2H), 7.08-7.14 (m, 4H), 7.23-7.34 (m, 5H), 8.12 (s, 1H), 10.24 (brs, 1H).

Mass (m/e, M$^+$): 409, 378, 335, 272

Example 7

Preparation of 4-[2-(4-fluoro-phenylsulfanyl)-acetylamino]-1-phenethyl-1H-pyrazole-3-carboxylic acid methyl ester 80 mg (0.2 mM) of the compound obtained in Preparative Example 3 was dissolved in 2 ml of tetrahydrofuran, to which 0.03 ml (0.3 mM, 1.5 eq) of 4-fluorobenzenethiol and 0.05 ml (0.3 mM, 1.5 eq) of triethylamine were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 88 mg (97.8%) of the title compound.

$^1$H NMR (300 MHz, CDCl$_3$) δ 3.18 (t, J=7.8 Hz, 2H), 3.70 (s, 2H), 3.99 (s, 3H), 4.35 (t, J=7.8 Hz, 2H), 6.99 (t, J=8.7 Hz, 2H), 7.12-7.14 (m, 2H), 7.22-7.28 (m, 3H), 7.42-7.46 (m, 2H), 8.10 (s, 1H), 10.16 (brs, 1H).

Mass (m/e, M$^+$): 413, 381, 363, 339

Example 8

Preparation of 4-[2-(2-pyridylsulfanyl)-acetylamino]-1-phenethyl-1H-pyrazole-3-carboxylic acid methyl ester 270 mg (0.74 mM) of the compound obtained in Preparative Example 3 was dissolved in 4 ml of tetrahydrofuran, to which 123 mg (1.1 mM, 1.5 eq) of 2-mercaptopyridine and 0.15 ml (1.1 mM, 1.5 eq) of triethylamine were added dropwise, and the resulting mixture was stirred under a nitrogen atmosphere for 2 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 283 mg (96.9%) of the title compound.

$^1$H NMR (300 MHz, CDCl$_3$) δ 3.16 (t, J=7.8 Hz, 2H), 3.93 (s, 3H), 3.99 (s, 2H), 4.34 (t, J=7.8 Hz, 2H), 7.06 (d, J=5.1 Hz, 1H), 7.13 (d, J=7.5 Hz, 2H), 7.22-7.28 (m, 4H), 7.50 (d, J=5.1 Hz, 1H), 8.19 (s, 1H), 8.63 (d, J=5.1 Hz, 1H), 10.41 (brs, 1H).

Mass (m/e, M$^+$): 396, 365, 321

Example 9

Preparation of 4-[2-(2-pyridylsulfinyl)-acetylamino]-1-phenethyl-1H-pyrazole-3-carboxylic acid methyl ester 100 mg (0.25 mM) of the compound obtained in Example 7 was dissolved in 2 ml of methylene chloride, to which 65 mg (0.38 mM, 1.5 eq) of 2-chloroperbenzoic acid was added dropwise, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:2), to obtain 63 mg (60.6%) of the title compound.

$^1$H NMR (300 MHz, CDCl$_3$) δ 3.16 (t, J=7.8 Hz, 2H), 3.86 (d, J=14.4 Hz, 1H), 4.02 (s, 3H), 4.26 (d, J=14.4 Hz, 1H), J=7.8 Hz, 2H), 7.11 (d, J=7.2 Hz, 2H), 7.22-7.28 (m, 3H), 7.39 (t, J=5.4 Hz, 1H), 7.92 (td, J=8.4 Hz, 1.5 Hz, 1H), 8.01 (d, J=8.4 Hz, 1H), 8.03 (s, 1H), 8.66 (d, J=4.2 Hz, 1H), 9.97 (brs, 1H).

Mass (m/e, M$^+$): 412, 393, 364, 322

Example 10

Preparation of 4-[2-(2-pyridylsulfonyl)-acetylamino]-1-phenethyl-1H-pyrazole-3-carboxylic acid methyl ester 100 mg (0.25 mM) of the compound obtained in Example 8 was dissolved in 2 ml of methylene chloride, to which 130 mg (0.75 mM, 3.0 eq) of 3-chloroperbenzoic acid was added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:2), to obtain 96 mg (88.9%) of the title compound.

$^1$H NMR (300 MHz, CDCl$_3$) δ 3.16 (t, J=7.8 Hz, 2H), 3.99 (s, 3H), 4.33 (t, J=7.8 Hz, 2H), 4.55 (s, 2H), 7.11 (dd, J=7.2, 1.5 Hz, 2H), 7.21-7.28 (m, 3H), 7.60 (dd, J=4.8, 0.9 Hz, 1H), 7.97-8.10 (m, 3H), 8.80 (d, J=4.8 Hz, 1H), 10.03 (brs, 1H).

Mass (m/e, M$^+$): 428, 397, 364, 322

Example 11

Preparation of 4-[2-(3,4-dimethyl-phenylsulfanyl)-acetylamino]-1-phenethyl-1H-pyrazole-3-carboxylic acid methyl ester 80 mg (0.2 mM) of the compound obtained in Preparative Example 3 was dissolved in 2 ml of tetrahydrofuran, to which 0.04 ml (0.3 mM, 1.5 eq) of 3,4-dimethylbenzenethiol and 0.05 ml (0.3 mM, 1.5 eq) of triethylamine were added dropwise, and the resulting mixture was stirred under a nitrogen atmosphere for 30 minutes. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 91 mg (98.9%) of the title compound.

$^1$H NMR (300 MHz, CDCl$_3$) δ 2.20 (s, 6H), 3.18 (t, J=7.8 Hz, 2H), 3.72 (s, 2H), 4.00 (s, 3H), 4.35 (t, J=7.8 Hz, 2H), 7.04 (d, J=7.8 Hz, 1H), 7.12-7.29 (m, 7H), 8.12 (s, 1H), 10.24 (brs, 1H).

Mass (m/e, M$^+$): 423, 319, 245

Example 12

Preparation of 4-[2-(4-bromo-phenylsulfanyl)-acetylamino]-1-benzyl-1H-pyrazole-3-carboxylic acid methyl ester 33 mg (0.094 mM) of the compound obtained in Preparative Example 6 was dissolved in 1 ml of tetrahydrofuran, to which 21 mg (0.11 mM) of 4-bromobenzenethiol and 17 μl (0.12 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 33 mg (77%) of the title compound.

$^1$H NMR (300 MHz, CDCl$_3$) δ 3.72 (s, 2H), 3.98 (s, 3H), 5.32 (s, 2H), 7.28 (m, 5H), 7.32 (m, 4H), 8.16 (s, 1H).

Mass (m/e, M$^+$): 461, 459

Example 13

Preparation of 4-[2-phenylsulfanylacetylamino]-1-benzyl-1H-pyrazole-3-carboxylic acid methyl ester 58 mg (0.16 mM) of the compound obtained in Preparative Example 6 was dissolved in 2 ml of tetrahydrofuran, to which 20 μl (0.19 mM) of benzenethiol and 29 μl (0.21 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 59 mg (94%) of the title compound.

$^1$H NMR (300 MHz, CDCl$_3$) δ 3.75 (s, 2H), 4.11 (s, 3H), 5.31 (s, 2H), 7.18 (m, 10H), 8.17 (s, 1H), 10.26 (br, NH).

Mass (m/e, M$^+$): 381

Example 14

Preparation of 4-[2-(4-bromo-phenylsulfanyl)-acetylamino]-1-methyl-1H-pyrazole-3-carboxylic acid methyl ester 70 mg (0.25 mM) of the compound obtained in Preparative Example 9 was dissolved in 2 ml of tetrahydrofuran, to which 57 mg (0.30 mM) of 4-bromobenzenethiol and 45 μl (0.33 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 76 mg (80%) of the title compound.

$^1$H NMR (300 MHz, CDCl$_3$) δ 3.75 (s, 2H), 3.94 (s, 3H), 3.97 (s, 3H), 7.29 (d, 2H), 7.40 (dd, 2H), 8.18 (s, 1H), 10.14 (br, NH).

Mass (m/e, M$^+$): 384 (Br79), 386 (Br81)

Example 15

Preparation of 4-[2-phenylsulfanylacetylamino]-1-methyl-1H-pyrazole-3-carboxylic acid methyl ester 100 mg (0.36 mM) of the compound obtained in Preparative Example 9 was dissolved in 5 ml of tetrahydrofuran, to which 44 μl (0.43 mM) of benzenethiol and 65 μl (0.47 mM) of triethylamine were added dropwise, and the resulting mixture was stirred under a nitrogen atmosphere for a day. The solvent was distilled off under reduced pressure, and the resulting solution was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 90 mg (82%) of the title compound.

$^1$H NMR (300 MHz, CDCl$_3$) δ 3.78 (s, 2H), 3.93 (s, 3H), 3.96 (s, 3H), 7.22 (m, 3H), 7.40 (d, 2H), 8.20 (s, 1H), 10.23 (br, NH).

Mass (m/e, M$^+$): 306 (M$^{+1}$)

Example 16

Preparation of 4-[2-(4-bromo-phenylsulfanyl)-acetylamino]-2-phenethyl-2H-pyrazole-3-carboxylic acid methyl ester 24 mg (0.07 mM) of the compound obtained in Preparative Example 12 was dissolved in 1 ml of tetrahydrofuran, to which 16 mg (0.09 mM) of 4-bromobenzenethiol and 10 μl (0.09 mM) of triethylamine were added dropwise, and the resulting mixture was stirred under a nitrogen atmosphere for 4 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 28 mg (88.1%) of the title compound.

$^1$H NMR (300 MHz, CDCl$_3$) δ 3.07 (t, J=7.8 Hz, 2H), 3.76-3.87 (m, 5H), 4.68 (t, J=7.8 Hz, 2H), 7.11-7.43 (m, 9H), 8.31 (s, 1H), 9.98 (brs, 1H).

Mass (m/e, M$^+$): 476, 371, 334

Example 17

Preparation of 4-[2-(4-bromo-phenylsulfanyl)-acetylamino]-2-methyl-2H-pyrazole-3-carboxylic acid methyl ester 50 mg (0.18 mM) of the compound obtained in Preparative Example 15 was dissolved in 2 ml of tetrahydrofuran, to which 41 mg (0.22 mM) of 4-bromobenzenethiol and 32 μl (0.23 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 58 mg (82%) of the title compound.

$^1$H NMR (300 MHz, CDCl$_3$) δ 3.76 (s, 2H), 3.94 (s, 3H), 4.11 (s, 3H), 7.20 (dd, 2H), 7.40 (dd, 2H), 8.25 (s, 1H), 10.00 (br, NH).

Mass (m/e, M$^+$): 306 (M$^{+1}$)

Example 18

Preparation of 4-[3-(4-bromo-phenylsulfanyl)-acetylamino]-1-phenethyl-1H-pyrazole-3-carboxylic acid methyl ester 200 mg (0.67 mM) of the compound obtained in Preparative Example 17 was dissolved in 7 ml of tetrahydrofuran, to which 165 mg of 4-bromobenzenethiol and 0.14 ml of triethylamine were added dropwise, and the resulting mixture was stirred under a nitrogen atmosphere for a day. The solvent was distilled off under reduced pressure, and the resulting solution was extracted with ethyl acetate and brine. The organic solvent layer was dried over anhydrous sodium sulfate, filtered, and then distilled under reduced pressure. The resulting impure compound was purified by column chromatography (hexane:ethyl acetate=4:1), to obtain 271 mg (82%) of the title compound.

$^1$H NMR (300 MHz, CDCl$_3$) δ 2.70 (t, 2H), 3.16-3.27 (m, 4H), 3.97 (s, 3H), 4.38 (t, 2H), 7.15 (d, 2H), 7.21-7.32 (m, 5H), 7.42 (d, 2H), 8.11 (s, 1H), 9.01 (br, NH).

Mass (m/e, M$^+$): 488, 419, 385

Example 19

Preparation of 5-[2-(4-bromo-phenylsulfanyl)-acetylamino]-1-phenethyl-1H-pyrazole-4-carboxylic acid ethyl ester 30 mg (0.08 mM) of the compound obtained in Preparative Example 19 was dissolved in 1 ml of tetrahydrofuran, to which 18 mg (0.096 mM) of 4-bromobenzenethiol and 14 μl (0.10 mM) of triethylamine were added dropwise, and the resulting mixture was stirred under a nitrogen atmosphere for a day. The solvent was distilled off under reduced pressure, and the resulting solution was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 33 mg (85%) of the title compound.

$^1$H NMR (300 MHz, CDCl$_3$) δ 1.25-1.34 (m, 3H), 3.17 (t, J=7.2 Hz, 2H), 3.80 (s, 2H), 4.24-4.33 (m, 4H), 7.10 (d, J=7.5 Hz, 2H), 7.23-7.31 (m, 5H), 7.38-7.42 (m, 2H), 7.49 (s, 1H), 10.39 (brs, 1H).

Mass (m/e, M$^+$): 486

Example 20

Preparation of 4-[2-(4-bromo-phenylsulfanyl)-2-phenyl-acetylamino]-1-phenethyl-1H-pyrazole-3-carboxylic acid methyl ester 100 mg (0.23 mM) of the compound obtained in Preparative Example 20 was dissolved in 3 ml of tetrahydrofuran, to which 52 mg (0.28 mM) of 4-bromobenzenethiol and 48 μl (0.35 mM) of triethylamine were added dropwise, and the resulting mixture was stirred under a nitrogen atmosphere for a day. The solvent was distilled off under reduced pressure, and the resulting solution was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 110 mg (87%) of the title compound.

$^1$H NMR (300 MHz, CDCl$_3$) δ 3.14 (t, 2H), 3.99 (s, 3H), 4.31 (t, 2H), 5.00 (s, 1H), 7.11 (d, 1H), 7.23-7.45 (m, 13H), 8.10 (s, 1H), 10.14 (s, NH).

Mass (m/e, M$^+$): 549, 551

Example 21

Preparation of 5-[2-(4-bromo-phenylsulfanyl)-acetylamino]-1-methyl-1H-pyrazole-3-carboxylic acid methyl ester 65 mg (0.24 mM) of the compound obtained in Preparative Example 23 was dissolved in 5 ml of tetrahydrofuran, to which 53 mg (0.22 mM) of 4-bromobenzenethiol and 39 μl (0.22 mM) of triethylamine were added dropwise, and the resulting mixture was stirred under a nitrogen atmosphere for a day. The solvent was distilled off under reduced pressure, and the resulting solution was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 77 mg (83%) of the title compound.

$^1$H NMR (300 MHz, CDCl$_3$) δ 9.02 (brs, 1H, N—H), 7.40 (d, 2H, J=8.7 Hz, ArH), 7.18-7.21 (m, 3H, ArH), 4.06 (s, 3H, OCH$_3$), 3.87 (s, 3H, N—CH$_3$), 3.74 (s, 2H, COCH$_2$).

Mass (m/e, M$^+$): 384

Example 22

Preparation of 1-methyl-5-(2-phenylsulfanyl-acetylamino)-1H-pyrazole-3-carboxylic acid methyl ester 50 mg (0.18 mM) of the compound obtained in Preparative Example 23 was dissolved in 5 ml of tetrahydrofuran, to which 23 μl (0.22 mM) of benzenethiol and 31 μl (0.22 mM) of triethylamine were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 52 mg (95%) of the title compound.

$^1$H NMR (300 MHz, CDCl$_3$) δ 9.07 (brs, 1H, N—H), 7.20-7.35 (m, 6H, ArH), 4.05 (s, 3H, OCH$_3$), 3.86 (s, 3H, N—CH$_3$), 3.76 (s, 2H, COCH$_2$).

Mass (m/e, M$^+$): 305

Example 23

Preparation of 4-[2-(4-bromo-phenylsulfanyl)-acetylamino]-1-phenethyl-1H-pyrazole-3-carboxylic acid 100 mg (0.2 mM) of the compound obtained in Example 1 was dissolved in 1 ml of methanol to which 0.3 ml (0.3 mM, 1.5 eq) of 1N sodium hydroxide was added dropwise, and the resulting mixture was heated with stirring under a nitrogen atmosphere for 1 hour. The resultant was acidified with 1N hydrochloric acid solution, and extracted with ethyl acetate and brine. The organic solvent layer was dried over anhydrous sodium sulfate, filtered, and then distilled under reduced pressure, to obtain 90 mg (91.5%) of the title compound.

$^1$H NMR (300 MHz, DMSO-d$_6$) δ 3.21 (t, J=7.3 Hz, 2H), 3.98 (s, 2H), 4.45 (t, J=7.3 Hz, 2H), 7.21-7.33 (m, 5H), 7.40-7.42 (m, 2H), 7.53-7.56 (m, 2H), 8.18 (s, 1H).

Mass (m/e, M$^+$): 460, 239, 231

Example 24

Preparation of 2-(4-bromo-phenylsulfanyl)-N-[3-(4,5-dihydro-oxazol-2-yl)-1-phenethyl-1H-pyrazol-4-yl]-acetamide 380 mg (0.83 mM) of the compound obtained in Example 23 was dissolved in 1 ml of tetrahydrofuran to which 356 mg (1.65 mM) of di(2-pyridyl (0.1 equivalent)) carbonate and 10 mg (0.08 mM) of dimethylaminopyridine were added dropwise, and the resulting mixture was stirred under a nitrogen atmosphere for 30 minutes. Subsequently, 0.17 ml (1.20 mM) of triethylamine and 144 mg (1.20 mM) of 2-chloroethylamine were added thereto, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 426 mg (99%) of the title compound.

$^1$H NMR (300 MHz, CDCl$_3$) δ 3.16 (t, J=7.8 Hz, 2H), 3.70-3.82 (m, 6H), 4.28 (t, J=7.8 Hz, 2H), 7.11-7.41 (m, 9H), 8.06 (s, 1H), 10.49 (brs, 1H).

Mass (m/e, M$^+$): 522, 486, 283, 105

300 mg (0.58 mM) of 4-[2-(4-bromo-phenylsulfanyl)-acetylamino]-1-phenethyl-1H-pyrazole-3-carboxylic acid (2-chloro-ethyl)-amide compound obtained above was dissolved in 3 ml of tetrahydrofuran, to which 0.15 ml (0.99 mM) of DBU was added dropwise, and the resulting mixture was heated to reflux under a nitrogen atmosphere for 3 hours. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 258 mg (92%) of the title compound.

$^1$H NMR (300 MHz, CDCl$_3$) δ 3.16 (t, J=7.8 Hz, 2H), 3.70-3.82 (m, 6H), 4.28 (t, J=7.8 Hz, 2H), 7.11-7.41 (m, 9H), 8.06 (s, 1H), 10.49 (brs, 1H).

Mass (m/e, M$^+$): 486, 283, 269

Example 25

Preparation of 4-[2-(4-bromo-phenylsulfanyl)-acetylamino]-1-phenethyl-1H-pyrazole-3-carboxylic acid amide 113 mg (0.3 mM) of the compound obtained in Example 23 was dissolved in 1 ml of tetrahydrofuran to which 60 μl (0.7 mM) of oxalyl chloride was added dropwise, and the resulting mixture was stirred under a nitrogen atmosphere for 30 minutes. Subsequently, 70 μl of NH$_4$OH was added thereto, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=2:1), to obtain 21 mg (19%) of the title compound.

$^1$H NMR (300 MHz, CDCl$_3$) δ 3.15 (t, J=7.8 Hz, 2H), 3.72 (s, 2H), 4.28 (t, J=7.8 Hz, 2H), 5.50 (brs, 1H), 6.67 (brs, 1H), 7.11 (d, J=7.8 Hz, 2H), 7.21-7.41 (m, 7H), 8.06 (s, 1H), 10.48 (brs, 1H).

Mass (m/e, M$^+$): 459

Example 26

Preparation of 2-(4-bromo-phenylsulfanyl)-N-(3-hydroxymethyl-1-phenethyl-4H-pyrazol-4-yl)-acetamide 150 mg (0.3 mM) of the compound obtained in Example 1 was dissolved in 2 ml of tetrahydrofuran to which 62 mg (0.9 mM) of lithium aluminum hydride was added dropwise at 0, and the resulting mixture was stirred at room temperature under a nitrogen atmosphere for 1 hour. After the reaction was terminated, the resultant was acidified with 1N hydrochloric acid solution, extracted with ethyl acetate and brine. The organic solvent layer was dried over anhydrous sodium sulfate, filtered, and then distilled under reduced pressure, to obtain 96 mg (68.1%) of the title compound.

$^1$H NMR (300 MHz, CDCl$_3$) δ 2.04 (t, J=5.7 Hz, 1H), 3.11 (t, J=7.8 Hz, 2H), 3.73 (s, 2H), 4.19 (t, J=7.8 Hz, 2H), 4.75 (d, J=5.7 Hz, 2H), 7.12-7.32 (m, 7H), 7.40-7.43 (m, 2H), 7.86 (s, 1H), 9.02 (brs, 1H), Mass (m/e, M$^+$): 446

Example 27

Preparation of 4-[3-phenyl-propionylamino]-1-phenethyl-4H-pyrazole-3-carboxylic acid methyl ester 200 mg (0.82 mM) of the compound obtained in Preparative Example 2 was dissolved in 8 ml of tetrahydrofuran, to which 0.16 ml (1.06 mM) of hydrocinnamoyl chloride and 0.17 ml (1.22 mM) of triethylamine were added dropwise, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 270 mg (87%) of the title compound.

$^1$H NMR (300 MHz, CDCl$_3$) δ 2.73 (t, 2H), 3.06 (t, 2H), 3.21 (t, 2H), 3.96 (s, 3H), 4.38 (t, 2H), 7.12-7.31 (m, 10H), 8.15 (s, 1H), 8.95 (brs, 1H).

Mass (m/e, M$^+$): 377, 345, 318

Example 28

Preparation of 4-[2-(4-bromophenoxy)-acetylamino]-1-phenethyl-1H-pyrazole-3-carboxylic acid methyl ester 120 mg (0.33 mM) of the compound obtained in Preparative Example 3 was dissolved in 10 ml of N,N-dimethylformamide, to which 90 mg (0.66 mM) of potassium carbonate and 68 mg (0.39 mM) of 4-bromophenol were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 104 mg (69%) of the title compound.

$^1$H NMR (300 MHz, CDCl$_3$) δ 3.22 (t, 2H), 3.99 (s, 3H), 4.41 (t, 2H), 4.60 (s, 2H), 6.93 (d, 2H), 7.14 (d, 2H), 7.21-7.32 (m, 3H), 7.46 (d, 2H), 8.15 (s, 1H), 10.04 (br, NH).

Mass (m/e, M$^+$): 458, 425, 398

Example 29

Preparation of 4-[2-(4-bromo-phenylamino)-acetylamino]-1-phenethyl-1H-pyrazole-3-carboxylic acid methyl ester 200 mg (0.55 mM) of the compound obtained in Preparative Example 3 was dissolved in 15 ml of N,N-dimethylformamide, to which 151 mg (1.1 mM, 2 eq) of potassium carbonate and 113 mg (0.66 mM, 1.2 eq) of 4-bromoaniline were added dropwise, and the resulting mixture was stirred under a nitrogen atmosphere for a day. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=3:1), to obtain 30 mg (12%) of the title compound.

$^1$H NMR (300 MHz, CDCl$_3$) δ 3.21 (t, 2H), 3.87 (s, 3H), 3.93 (d, 2H), 4.39 (t, 2H), 4.41-4.44 (d, 1H), 6.57 (d, 2H), 7.15 (d, 2H), 7.22-7.31 (m, 5H), 8.16 (s, 1H), 9.88 (br, NH).

Mass (m/e, M$^+$): 456, 426, 397

Example 30

Preparation of 2-(4-bromo-phenylsulfanyl)-N-(3-methoxymethyl-1-phenethyl-1H-pyrazol-4-yl)-acetamide 41 mg (0.12 mM) of the compound obtained in Preparative Example 28 was dissolved in 2 ml of tetrahydrofuran, to which 28 mg (0.15 mM, 1.3 eq) of 4-bromobenzenethiol and 0.02 ml (0.18 mM, 1.5 eq) of triethylamine were added dropwise, and the resulting mixture was stirred under a nitrogen atmosphere for 1 hour. The solvent was distilled off under reduced pressure, and the resultant was extracted with ethyl acetate and brine. The organic solvent layer was dried over anhydrous sodium sulfate, filtered, and then distilled under reduced pressure. The resulting impure compound was purified by column chromatography (hexane:ethyl acetate=1:1), to obtain 90 mg (97.8%) of the title compound.

$^1$H NMR (300 MHz, CDCl$_3$) δ 3.12 (t, J=7.8 Hz, 2H), 3.32 (s, 3H), 3.70 (s, 2H), 4.22 (t, J=7.8 Hz, 2H), 4.56 (s, 2H), 7.11-7.27 (m, 7H), 7.40-7.43 (m, 2H), 7.95 (s, 1H), 9.19 (brs, 1H).

Mass (m/e, M$^+$): 460

The aminopyrazole derivatives according to the present invention were assayed for various biochemical and pharmacological activities through the following experiments.

Experimental Example 1

Inhibitory Effect on Ischemic Cell Death

The aminopyrazole derivatives of the present invention were examined for ischemic cell death inhibitory effect in cells according to the following procedure.

Cardiomyocyte cell line H9c2 cells were cultured in DMEM (Dulbecco's modified Eagle's medium) supplemented with 10% fetal bovine serum and 1% penicillin/streptomycin (100× solution). The cells were grown in 35 mm dishes such that the number thereof becomes 1×10$^4$, and cultured at 37° C. for 48 hours in a CO$_2$ incubator. The cells were treated with 0.1% DMSO only (control), or the solutions dissolving the derivatives of Examples 1 to 30 (10 μM) in DMSO respectively. After 30 minutes, the cells were washed with PBS, and continuously treated with the DMSO solution (control) or the above solutions dissolving the derivatives together with chemical hypoxia solution (106 mM NaCl, 4.4 mM KCl, 1 mM MgCl$_2$, 38 mM NaHCO$_3$, 2.5 mM CaCl$_2$, 20 mM 2-deoxy glucose, 1 mM NaCN) for 1 to 2 hours, while evaluating the cell damage by microscope. At the time when the sufficient damage were observed, the cells were washed with 1 ml of PBS twice, and then treated to fix with 1 ml of 3.7% formaldehyde. The cells obtained were washed with 1 ml of PBS again, stained with DAPI, and then washed with 1 ml of PBS in three times. The cell death of the cells was observed by a fluorescence microscope, and the degree of the observed cell death was converted to percentages. The results were summarized in Table 2 below and FIG. 1.

TABLE 2

The Inhibitory Effect of Aminopyrazole Derivatives on the Ischemic Cell death

|  | Apoptosis (%) | Error |
|---|---|---|
| Control | 25.86385 | 0.723647 |
| Example 1 | 5.786328 | 0.55752 |
| Example 2 | 11.00814 | 0.117308 |
| Example 3 | 8.256101 | 1.91806 |
| Example 4 | 3.739943 | 0.235702 |
| Example 5 | 6.484921 | 0.429886 |
| Example 6 | 5.433503 | 0.053166 |
| Example 7 | 6.491977 | 0.816757 |
| Example 8 | 5.645198 | 0.909137 |
| Example 9 | 3.739943 | 0.324278 |
| Example 10 | 7.268192 | 0.08773 |
| Example 11 | 15.73599 | 2.27928 |
| Example 12 | 11.50209 | 0.155286 |
| Example 13 | 9.808531 | 0.185906 |
| Example 14 | 13.33678 | 0.2863 |
| Example 15 | 11.2904 | 0.04098 |
| Example 16 | 10.79644 | 0.467216 |
| Example 17 | 13.9013 | 0.200598 |
| Example 18 | 8.750056 | 0.903525 |
| Example 19 | 8.185537 | 0.149441 |
| Example 20 | 6.068587 | 0.056008 |
| Example 21 | 8.326666 | 0.136323 |
| Example 22 | 10.72588 | 0.781473 |
| Example 23 | 7.762147 | 0.265514 |
| Example 24 | 12.70169 | 0.502576 |
| Example 25 | 6.068587 | 0.010633 |
| Example 26 | 7.268192 | 1.654861 |
| Example 27 | 5.080678 | 0.131189 |
| Example 28 | 3.739943 | 0.102479 |
| Example 29 | 9.314576 | 0.457197 |
| Example 30 | 5.221808 | 0.349382 |

As shown in Table 2 and FIG. 1, the aminopyrazole derivatives of the present invention showed an inhibitory effect on ischemic cell death.

Formulations containing the compounds of the present invention as effective ingredients are illustrated in the following examples, but are not construed to limit the scope of the present invention.

Formulation Example 1

Tablet (Direct Compression)

After being sieved, 5.0 mg of a compound of the present invention was mixed with 14.1 mg of lactose, 0.8 mg of crospovidone USUF and 0.1 mg of magnesium stearate and compressed into tablet form.

Formulation Example 2

Tablet (Wetting Formula)

After being sieved, 5.0 mg of a compound of the present invention was mixed with 16.0 mg of lactose and 4.0 mg of starch. To a solution of 0.3 mg of polysolvate 80 in purified water, the mixture was added. After section to a fine size, the fine powder was dried, sieved, and mixed with 2.7 mg of colloidal silicon dioxide and 2.0 mg of magnesium stearate. Compression of the mixture gives a tablet.

Formulation Example 3

Powder and Capsule 5.0 mg of a compound of the present invention was sieved and mixed with 14.8 mg of lactose, 10.0 mg of polyvinyl pyrrolidone, and 0.2 mg of magnesium stearate. The mixture was filled in a hard gelatine capsule No. 5, using a suitable apparatus.

Formulation Example 4

Injection

An injection was prepared from 100 mg of a compound of the present invention, 180 mg of mannitol, 26 mg of $Na_2HPO_4 \cdot 12H_2O$ and 2974 mg of distilled water.

Industrial Applicability

As described hereinbefore, the aminopyrazole derivatives of the present invention can reduce an ischemic cell death significantly. Consequently, the pharmaceutical compositions of the present invention as well as the compounds can be effectively used for the prevention and treatment of ischemic diseases such as brain ischemia mediated by ischemic cell death, heart ischemia, diabetic cardiovascular disease, heart failure, myocardial hypertrophy, retinal ischemia, ischemic colitis, ischemic acute renal failure, stroke, head trauma, Alzheimer's disease, Parkinson's disease, neonatal hypoxia, glaucoma or diabetic neuropathy, and the protection of organs.

What is claimed is:

1. An Aminopyrazole compound of Formula 1, or a pharmaceutically acceptable salt thereof:

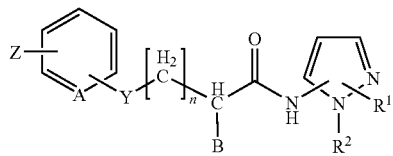

Formula 1 wherein
$R^1$ is $—CO_2R^3$, $—CH_2OR^3$, $—CONR^3R^4$ or

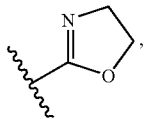

wherein $R^3$ and $R^4$ are, independently of each other, H, or straight, branched or cyclic $C_1$-$C_6$ alkyl;
$R^2$ is $—(CH_2)_2Ar$ wherein Ar is phenyl;
B is H, phenyl, or $C_1$-$C_3$ alkyl or halogen substituted phenyl;
n is an integer of 0 to 2;
Y is S, O, $CH_2$, SO, $SO_2$ or $NR^3R^4$ wherein $R^3$ and $R^4$ are, independently of each other, H, or straight, branched or cyclic $C_1$-$C_6$ alkyl;
Z is H, halogen, $OCH_3$, $NO_2$, $NH_2$, or straight, branched or cyclic $C_1$-$C_3$ alkyl; and
A is CH or N.

2. The aminopyrazole compound or a pharmaceutically acceptable salt according to claim 1, wherein
$R^1$ is $—CO_2R^3$, $—CH_2OR^3$, $—CONR^3R^4$ or

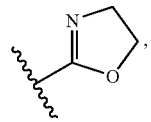

wherein $R^3$ and $R^4$ are, independently of each other, H, methyl or ethyl;
$R^2$ is $—(CH_2)_2Ar$ wherein Ar is phenyl;
B is H, phenyl, or $C_1$-$C_3$ alkyl or halogen substituted phenyl;
n is 0 or 1;
Y is S, O, $CH_2$, SO, $SO_2$ or $NR^3R^4$ wherein $R^3$ and $R^4$ are, independently of each other, H, or straight, branched or cyclic $C_1$-$C_6$ alkyl;
Z is H, halogen, $OCH_3$, $NO_2$, $NH_2$, or straight or branched $C_1$-$C_3$ alkyl; and
A is CH or N.

3. The aminopyrazole compound or a pharmaceutically acceptable salt according to claim 1, being selected from the group consisting of:

4-[2-(4-bromo-phenylsulfanyl)-acetylamino]-1-phenethyl-1H-pyrazole-3-carboxylic acid methyl ester;
4-[2-(phenylsulfanyl)-acetylamino]-1-phenethyl-1H-pyrazole-3-carboxylic acid methyl ester;
4-[2-(3-methoxy-phenylsulfanyl)-acetylamino]-1-phenethyl-1H-pyrazole-3-carboxylic acid methyl ester;
4-[2-(4-nitro-phenylsulfanyl)-acetylamino]-1-phenethyl-1H-pyrazole-3-carboxylic acid methyl ester;
4-[2-(2-amino-phenylsulfanyl)-acetylamino]-1-phenethyl-1H-pyrazole-3-carboxylic acid methyl ester;
4-[2-(4-methyl-phenylsulfanyl)-acetylamino]-1-phenethyl-1H-pyrazole-3-carboxylic acid methyl ester;
4-[2-(4-fluoro-phenylsulfanyl)-acetylamino]-1-phenethyl-1H-pyrazole-3-carboxylic acid methyl ester;
4-[2-(2-pyridylsulfanyl)-acetylamino]-1-phenethyl-1H-pyrazole-3-carboxylic acid methyl ester;
4-[2-(2-pyridylsulfinyl)-acetylamino]-1-phenethyl-1H-pyrazole-3-carboxylic acid methyl ester;
4-[2-(2-pyridylsulfonyl)-acetylamino]-1-phenethyl-1H-pyrazole-3-carboxylic acid methyl ester;
4-[2-(3,4-dimethyl-phenylsulfanyl)-acetylamino]-1-phenethyl-1H-pyrazole-3-carboxylic acid methyl ester;
4-[2-(4-bromo-phenylsulfanyl)-acetylamino]-2-phenethyl-2H-pyrazole-3-carboxylic acid methyl ester;
4-[3-(4-bromo-phenylsulfanyl)-acetylamino]-1-phenethyl-1H-pyrazole-3-carboxylic acid methyl ester;
5-[2-(4-bromo-phenylsulfanyl)-acetylamino]-1-phenethyl-1H-pyrazole-4-carboxylic acid ethyl ester;
4-[2-(4-bromo-phenylsulfanyl)-2-phenyl-acetylamino]-1-phenethyl-1H-pyrazole-3-carboxylic acid methyl ester;
4-[2-(4-bromo-phenylsulfanyl)-acetylamino]-1-phenethyl-1H-pyrazole-3-carboxylic acid;
2-(4-bromo-phenylsulfanyl)-N-[3-(4,5-dihydro-oxazol-2-yl)-1-phenethyl-1H-pyrazol-4-yl]-acetamide;
4-[2-(4-bromo-phenylsulfanyl)-acetylamino]-1-phenethyl-1H-pyrazole-3-carboxylic acid amide;
2-(4-bromo-phenylsulfanyl)-N-(3-hydroxymethyl-1-phenethyl-1H-pyrazol-4-yl)-acetamide;
4-[3-phenyl-propionylamino]-1-phenethyl-1H-pyrazole-3-carboxylic acid methyl ester;
4-[2-(4-bromo-phenoxy)-acetylamino]-1-phenethyl-1H-pyrazole-3-carboxylic acid methyl ester;

4-[2-(4-bromo-phenylamino)-acetylamino]-1-phenethyl-1H-pyrazole-3-carboxylic acid methyl ester; and 2-(4-bromo-phenylsulfanyl)-N-(3-methoxymethyl-1-phenethyl-1H-pyrazol-4-yl)-acetamide.

4. A process for preparing an aminopyrazole compound of Formula 1 comprising reacting an aminopyrazole compound of Formula 2 with a compound of Formula 3:

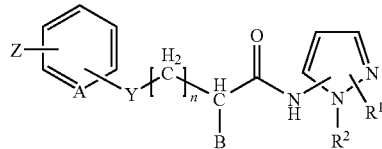

Formula 1

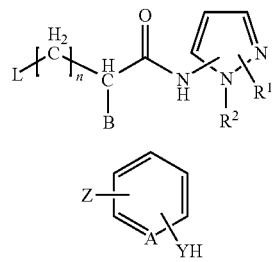

Formula 2

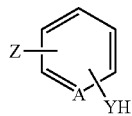

Formula 3 wherein $R^1$, $R^2$, B, n, Y, Z and A are as defined in claim 1, and L is a leaving group.

5. A pharmaceutical composition, containing the aminopyrazole compound of claim 1, or a pharmaceutically acceptable salt thereof.

* * * * *